United States Patent
Kurihara et al.

(10) Patent No.: US 6,423,729 B1
(45) Date of Patent: Jul. 23, 2002

(54) THERAPEUTIC OR PROPHYLACTIC AGENT FOR GLOMERULOPATHY

(75) Inventors: Hidetake Kurihara, Tokyo; Fumihiko Watanabe, Osaka; Yoshinori Tamura, Osaka; Toshihiro Sinosaki, Osaka, all of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/462,001

(22) PCT Filed: Jul. 17, 1998

(86) PCT No.: PCT/JP98/03226

§ 371 (c)(1), (2), (4) Date: Dec. 30, 1999

(87) PCT Pub. No.: WO99/04780

PCT Pub. Date: Feb. 4, 1999

(30) Foreign Application Priority Data

Jul. 22, 1997 (JP) .............................................. 9-195414

(51) Int. Cl.⁷ ..................... C07D 333/18; A61K 31/405
(52) U.S. Cl. ........................................ 514/364; 548/131
(58) Field of Search ........................... 548/131; 514/364

(56) References Cited

FOREIGN PATENT DOCUMENTS

| EP | 0 757 037 A2 | 2/1997 |
| EP | 757037 | 2/1997 |
| EP | 0 765 661 A2 | 4/1997 |
| EP | 0 757 984 A1 | 12/1997 |
| EP | 9 915 086 A1 | 5/1999 |
| EP | 0 950 656 A1 | 10/1999 |
| JP | 7 300426 | 11/1995 |
| JP | 9 87176 | 3/1997 |
| JP | 9 110864 | 4/1997 |
| WO | WO 95/35276 | 12/1995 |
| WO | WO 96/00214 | 1/1996 |
| WO | WO 97/05865 | 2/1997 |
| WO | 97/27174 | 7/1997 |
| WO | WO 97/27174 | 7/1997 |
| WO | WO 97/44315 | 11/1997 |
| WO | WO 97/45402 | 12/1997 |
| WO | WO 97/45402 | 1/1998 |
| WO | WO 98/03166 | 1/1998 |
| WO | WO 98/43963 | 8/1998 |

OTHER PUBLICATIONS

R.V. Ward et al., J. Biochem., vol. 278, "The purification of tissue inhibitor of metalloproteinases–2 from its 72 kDa progelatinase complex," pp. 179–187 (1991).

Y. Okada et al., Eur J. Biochem., vol. 194, Matrix metalloproteinase 2 from human rheumatoid synovial fibroblasts (Purification and activation of the precursor and enzymic properties), pp. 721–730 (1990).

Y. Okada et al., J. Bio. Chem., vol. 267, No. 30, "Matrix Metalloproteinase 9 (92–kDa Gelatinase/Type IV Collagenase) from HT 1080 Human Fibrosarcoma Cells," pp. 21712–21719 (1992).

C.G. Knight et al., FEBS, vol. 296, No. 3, "A novel coumarin–labelled peptide for sensitive continuous assays of the matrix metalloproteinases," pp. 263–266 (1992).

J.J.N., vol. 36, p. 106 (1994).

J.J.N., vol. 39, p. 220 (1997).

J.J.N., vol. 39, p. 300 (1997).

Albert Wolthuis et al., Am. J. Pathol., vol. 143, No. 4, "Cell Density Modulates Growth, Extracellular Matrix, and Protein Synthesis of Cultured Rat Mesangial Cells," pp. 1209–1219 (1993).

Yoshinori Tamura et al., J. Med. Chem., vol. 41, No. 4, "Highly Selective and Orally Active Inhibitors of type IV Collagenase (MMP–9 and MMP–2); N–Sulfonylamino Acid Derivatives," pp. 640–649 (1998).

*Primary Examiner*—Robert Gersil
(74) *Attorney, Agent, or Firm*—Foley & Lardner

(57) ABSTRACT

A composition for treating or preventing glomerulopathy which contains a compound of the formula (I):

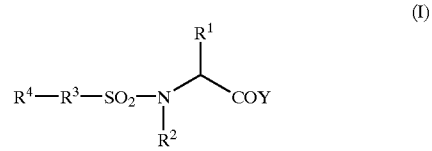

(I)

wherein, for example, $R^1$ and $R^2$ are each independently hydrogen atom, optionally substituted lower alkyl, optionally substituted aralkyl, etc.;

$R^3$ is 1,4-phenylene and 2,5-thiophendiyl;

$R^4$ is the substituents represented by the formula, etc.:

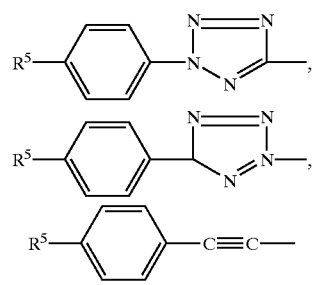

wherein $R^6$ is hydrogen atom, optionally substituted amino, etc.; and

Y is NHOH or OH, its optically active substance, their pharmaceutically acceptable salt, or hydrate thereof.

13 Claims, 3 Drawing Sheets

THERAPEUTIC OR PROPHYLACTIC AGENT FOR GLOMERULOPATHY

TECHNICAL FIELD

This invention relates to a composition for treating or preventing glomerulopathy, especially glomerulonephritis and diabetic nephropathy, having a superior antiproteinuric effect and to a novel compound having superior inhibitory activity for type IV collagenase and an antiproteinuric effect and a composition containing it for treating or preventing.

BACKGROUND ART

A glomerulus is organized by epithelial cells, mesangial cells, endothelial cells, and epithelial cells of Bowman's capsule. The glomerulus filtrates blood to produce a glomerular filtrate containing substantially the same components as plasma components of which molecular weight is 10,000 or less. Generally, the filtration is controlled not to leak essential substances in blood, especially serum protein, to urine.

Glomerulus damage causes the growth of mesangial cells which are one of the glomerulus component cells and the expansion of a neighbor extracellular matrix to increase the amount of urinary protein excretion. It is known that the increase of urinary protein excretion further lowers the renal function by leading glomerulopathy to damage of renal tubules. Therefore, the inhibition of the urinary protein excretion is expected to improve various diseases associated with glomerulopathy. Such damage is derived from not only a primary disease but also a systemic disease such as diabetes. However, initiation and progression mechanisms remain uncertain and a fundamental method for treatment is not established.

As the present treating method, symptomatic therapies are carried out, but they have many problems. For example, the immunosuppressants are used for patients of nephritis because many types of nephritis are considered to be caused by immunologic mechanism, but nephrotoxicity occurs by the prolonged administration. Though steroids are also administered to the patients of nephritis, some nephritis are resistant to them. Recently, it is proved that angiotensin converting enzyme inhibitors (antihypertensive agents) are useful for nephritis. However, the medicament for nephritis without a hypotensive effect is required.

Accordingly, pharmacotherapy of glomerulopathy has been in a trial and error stage. The treatment of glomerulopathy is made more difficult by the fact that the cause of glomerulopathy is not all alike and clinical course full of variety can not easily be prospected.

As a treating agent for nephritis other than the above mentioned medicament, compounds described in JP-A-9-87176 are exemplified.

Compounds similar to those of the present invention are described in WO97/27174, EP0757984 A1, EP0757037 A2, WO97/45402, WO97/44315, WO96/00214, WO95/35276, and WO97/05865.

DISCLOSURE OF INVENTION

In the above situation, the inventors of the present invention have studied on the medicament which can inhibit the initiation and progression of glomerulopathy such as glomerulonephritis and diabetic nephropathy or decrease urinary protein excretion.

The inventors of the present invention made glomerulopathy model rats which leak urine proteins by using a nephritogenic antibody and searched for compounds inhibiting the initiation and progression of the damage of model rats. In result, the inventors of the present invention found that some sulfonamide derivatives inhibited the initiation and progression of glomerulopathy, especially glomerulonephritis and diabetic nephropathy through the inhibition of protein excretion and they are useful treating or preventing them.

The present invention relates to i) to xxxiv) represented below.

i) A composition for treating or preventing glomerulopathy which contains a compound of the formula (I):

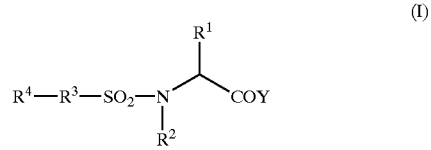

(I)

wherein $R^1$ and $R^2$ are each independently hydrogen atom, optionally substituted lower alkyl, optionally substituted aryl, optionally substituted aralkyl, optionally substituted heteroayl, or optionally substituted heteroarylalkyl;

$R^3$ is 1,4-phenylene or 2,5-thiophendiyl;

$R^4$ is a substituent represented by the formula:

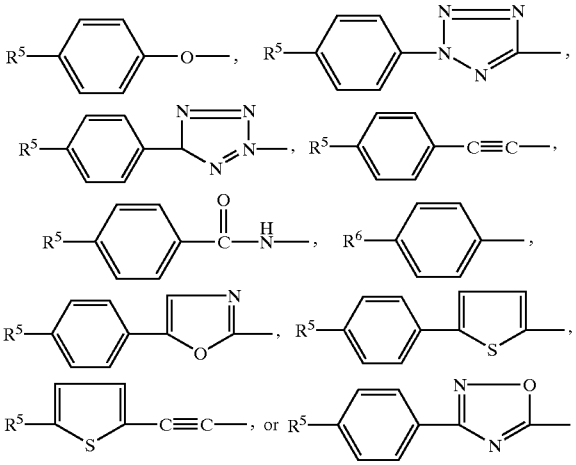

wherein $R^5$ is hydrogen atom, hydroxy, optionally substituted lower alkyloxy, mercapto, lower alkylthio, cycloalkyl, halogen, carboxy, lower alkyloxycarbonyl, nitro, cyano, lower holoalkyl, aryloxy, optionally substituted amino, guanidino, optionally substituted lower alkyl, lower alkenyl, lower alkynyl, acyl, acyloxy, $-CONR^A R^B$, $-N(R^C)COR^D$ (wherein $R^A$, $R^B$, and $R^C$ are the same or different selected from hydrogen atom, lower alkyl, or aralkyl; $R^D$ is lower alkyl, aryl, and aralkyl), optionally substituted non-aromatic heterocyclic group, or optionally substituted heteroaryl;

$R^6$ is optionally substituted lower alkyl, cycloalkyl, lower alkyloxy, halogen, lower alkylthio, optionally substituted amino, carboxy, lower alkyloxycarbonyl, aryloxy, phenyl, optionally substituted non-aromatic heterocyclic group, or optionally substituted heteroaryl; and Y is NHOH or OH, its optically active substance, their pharmaceutically acceptable salt, or hydrate thereof.

ii) A composition for treating or preventing glomerulopathy which contains a compound of the formula (II):

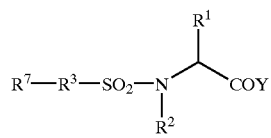

(II)

wherein $R^1$, $R^2$, and $R^3$ are as defined above:
$R^7$ is a substitution represented by the formula:

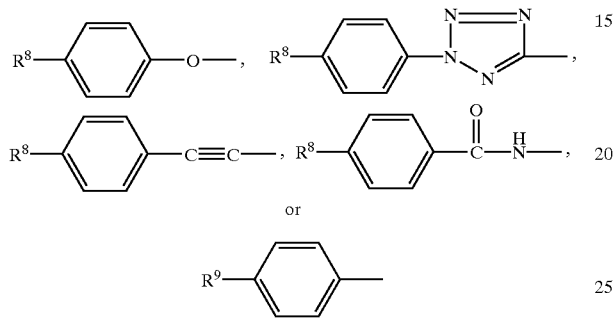

or wherein $R^8$ is hydrogen atom, hydroxy, lower alkyloxy, mercapto, lower alkylthio, cycloalkyl, halogen, carboxy, lower alkyloxycarbonyl, nitro, cyano, lower haloalkyl, aryloxy, optionally substituted amino, guanidino, optionally substituted lower alkyl, lower alkenyl, lower alkynyl, alkanoyl, acyloxy, or optionally substituted heteroaryl;

$R^9$ is optionally substituted lower alkyl, cycloalkyl, carboxy, lower alkyloxycarbonyl, aryloxy, or phenyl; and Y is NHOH or OH, its optically active substance, their pharmaceutically acceptable salt, or hydrate thereof.

iii) A composition for treating or preventing glomerulopathy which contains a compound of the formula (I):

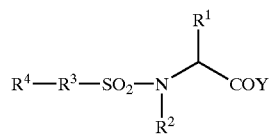

(I)

wherein $R^1$, $R^2$, and $R^3$ are as defined above;
$R^4$ is a substituent represented by the formula:

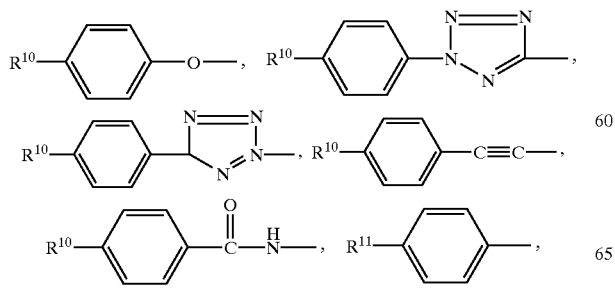

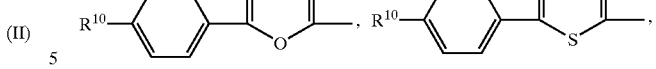

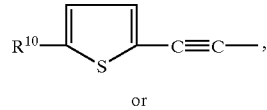

or

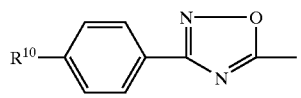

wherein $R^{10}$ is hydrogen atom, optionally substituted lower alkyloxy, lower alkylthio, halogen, optionally substituted amino, optionally substituted lower alkyl, or optionally substituted non-aromatic heterocyclic group;

$R^{11}$ is optionally substituted lower alkyl, lower alkylthio, halogen, optionally substituted amino, phenyl, optionally substituted non-aromatic heterocyclic group, or optionally substituted heteroaryl; and Y is NHOH or OH, its optically active substance, their pharmaceutically acceptable salt, or hydrate thereof.

iv) A composition for treating or preventing glomerulopathy which contains a compound of the formula (II):

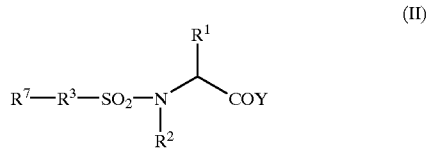

(II)

wherein $R^1$, $R^2$, and $R^3$ are as defined above;
$R^7$ is a substituent represented by the formula:

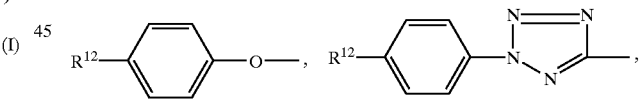

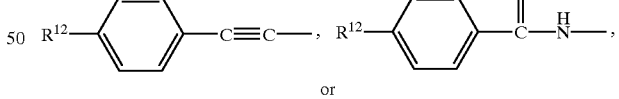

or

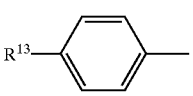

wherein $R^{12}$ is hydrogen atom, halogen, nitro, optionally substituted lower alkyl, lower alkyloxy, or lower alkylthio;

$R^{13}$ is optionally substituted lower alkyl or phenyl; and

Y is NHOH or OH, its optically active substance, their pharmaceutically acceptable salt, or hydrate thereof.

v) A composition for treating or preventing glomerulopathy which contains a compound of the formula (III):

(III)

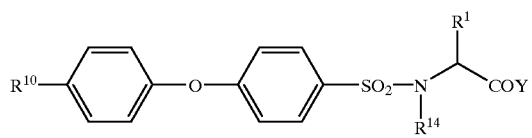

wherein $R^1$, $R^{10}$, and Y are as defined above; and $R^{14}$ is hydrogen atom or lower alkyl, its optically active substance, their pharmaceutically acceptable salt, or hydrate thereof.

vi) A composition for treating or preventing glomerulopathy which contains a compound of the formula (IV):

(IV)

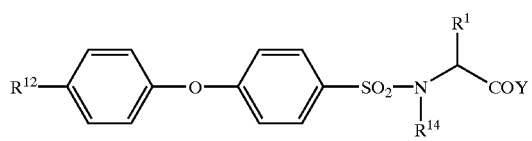

wherein $R^1$, $R^{12}$, $R^{14}$, and Y are as defined above, its optically active substance, their pharmaceutically acceptable salt, or hydrate thereof.

vii) A composition for treating or preventing glomerulopathy which contains a compound of the formula (V):

(V)

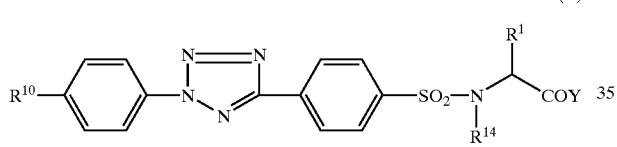

wherein $R^1$, $R^{10}$, $R^{14}$, and Y are as defined above, its optically active substance, their pharmaceutically acceptable salt, or hydrate thereof.

viii) A composition for treating or preventing glomerulopathy which contains a compound of the formula (VI):

(VI)

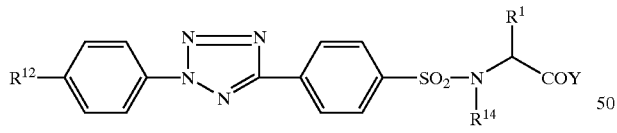

wherein $R^1$, $R^{12}$, $R^{14}$, and Y are as defined above, its optically active substance, their pharmaceutically acceptable salt, or hydrate thereof.

ix) A composition for treating or preventing glomerulopathy which contains a compound of the formula (VII):

(VII)

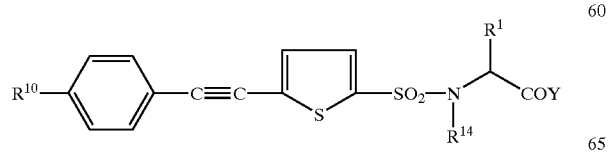

wherein $R^1$, $R^{10}$, $R^{14}$, and Y are as defined above, its optically active substance, their pharmaceutically acceptable salt, or hydrate thereof.

x) A composition for treating or preventing glomerulopathy which contains a compound of the formula (VIII):

(VIII)

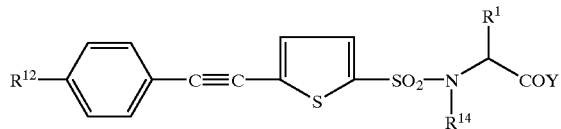

wherein $R^1$, $R^{12}$, $R^{14}$, and Y are as defined above, its optically active substance, their pharmaceutically acceptable salt, or hydrate thereof xi) A composition for treating or preventing glomerulopathy which contains a compound of the formula (IX):

(IX)

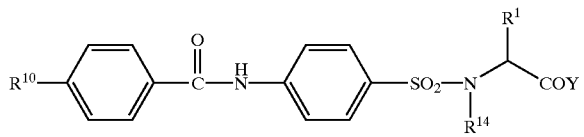

wherein $R^1$, $R^{10}$, $R^{14}$, and Y are as defined above, its optically active substance, their pharmaceutically acceptable salt, or hydrate thereof.

xii) A composition for treating or preventing glomerulopathy which contains a compound of the formula (X):

(X)

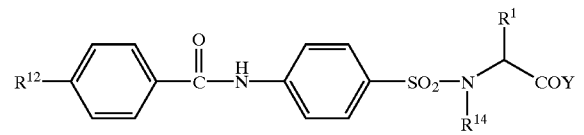

wherein $R^1$, $R^{12}$, $R^{14}$, and Y are as defined above, its optically active substance, their pharmaceutically acceptable salt, or hydrate thereof xiii) A composition for treating or preventing glomerulopathy which contains a compound of the formula (XI):

(XI)

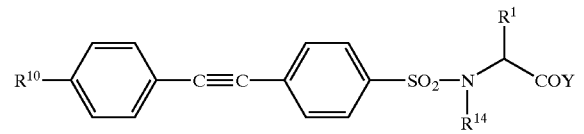

wherein R¹, R¹⁰, R¹⁴, and Y are as defined above, its optically active substance, their pharmaceutically acceptable salt, or hydrate thereof xiv) A composition for treating or preventing glomerulopathy which contains a compound of the formula (XII):

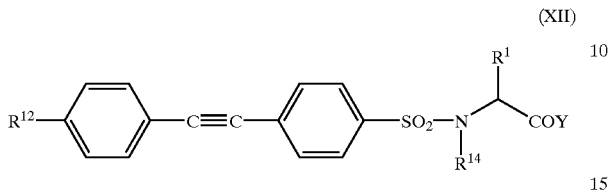

(XII)

wherein R¹, R¹², R¹⁴, and Y are as defined above, its optically active substance, their pharmaceutically acceptable salt, or hydrate thereof xv) A composition for treating or preventing glomerulopathy which contains a compound of the formula (XIII):

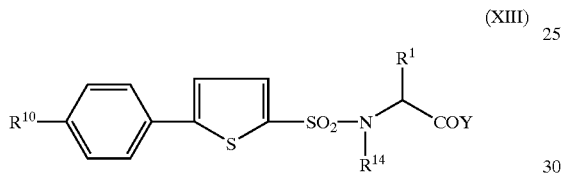

(XIII)

wherein R¹, R¹⁰, R¹⁴, and Y are as defined above, its optically active substance, their pharmaceutically acceptable salt, or hydrate thereof.

xvi) A composition for treating or preventing glomerulopathy which contains a compound of the formula (XIV):

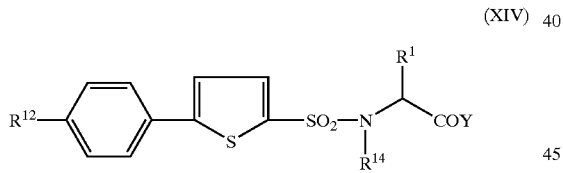

(XIV)

wherein R¹, R¹², R¹⁴, and Y are as defined above, its optically active substance, their pharmaceutically acceptable salt, or hydrate thereof.

xvii) A composition for treating or preventing glomerulopathy which contains a compound of the formula (XV):

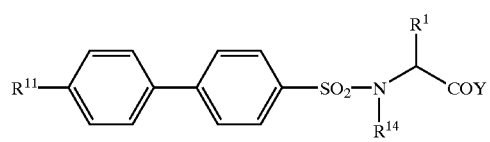

(XV)

wherein R¹, R¹¹, R¹⁴, and Y are as defined above, its optically active substance, their pharmaceutically acceptable salt, or hydrate thereof xviii) A composition for treating or preventing glomerulopathy which contains a compound of the formula (XVI):

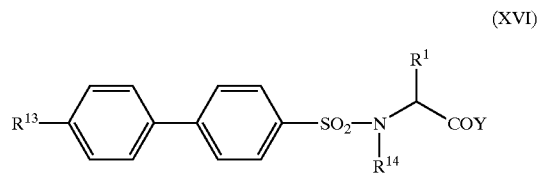

(XVI)

wherein R¹, R¹³, R¹⁴, and Y are as defined above, its optically active substance, their pharmaceutically acceptable salt, or hydrate thereof.

xix) The composition for treating or preventing glomerulopathy of any one of above i) to xviii), wherein RI is hydrogen atom, methyl, i-propyl, i-butyl, optionally substituted benzyl, optionally substituted indol-3-ylmethyl, or phenylaminocarbonyl-ethyl.

xx) The composition for treating or preventing glomerulopathy of any one of above i) to xviii), wherein R¹ is i-propyl, benzyl, or indol-3-ylmethyl.

xxi) The composition for treating or preventing glomerulopathy of any one of above i) to xx), wherein R² and R¹⁴ are hydrogen atom.

xxii) The composition for treating or preventing glomerulopathy of any one of above i) to xxi), wherein Y is OH.

xxiii) The composition for treating or preventing glomerulopathy of any one of above i) to xxii), wherein glomerulopathy is glomerulonephritis.

xxiv) The composition for treating or preventing glomerulopathy of any one of above i) to xxii), wherein glomerulopathy is diabetic nephropathy.

xxv) A compound of the formula (XVII):

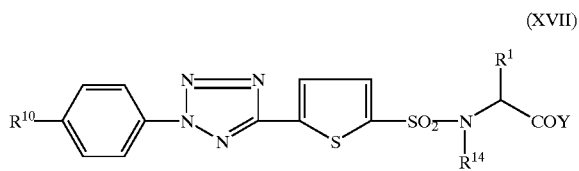

(XVII)

wherein R¹, R¹⁰, R¹⁴, and Y are as defined above, its optically active substance, their pharmaceutically acceptable salt, or hydrate thereof.

xxvi) A compound of the formula (XVIII):

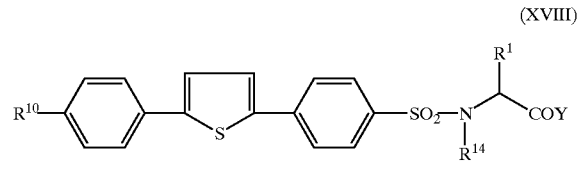

(XVIII)

wherein R¹, R¹⁰, R¹⁴, and Y are as defined above, its optically active substance, their pharmaceutically acceptable salt, or hydrate thereof.

xxvii) A compound of the formula (XIX):

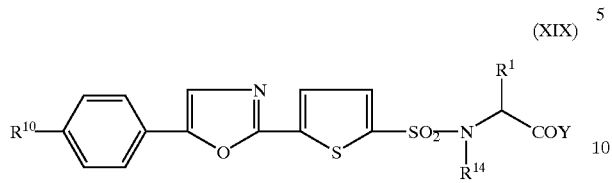

(XIX)

wherein $R^1$, $R^{10}$, $R^{14}$, and Y are as defined above, its optically active substance, their pharmaceutically acceptable salt, or hydrate thereof.

xxviii) A compound of the formula (XX):

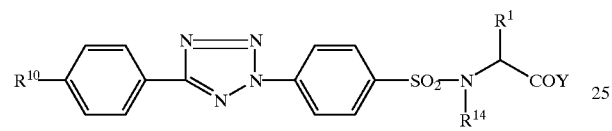

(XX)

wherein $R^1$, $R^{10}$, $R^{14}$, and Y are as defined above, its optically active substance, their pharmaceutically acceptable salt, or hydrate thereof.

xxix) A compound of the formula (XX):

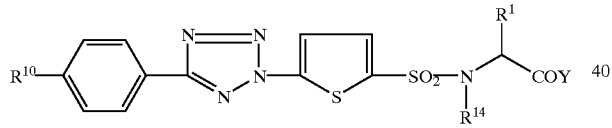

(XXI)

wherein $R^1$, $R^{10}$, $R^{14}$, and Y are as defined above, its optically active substance, their pharmaceutically acceptable salt, or hydrate thereof.

xxx) A compound of the formula (XXII):

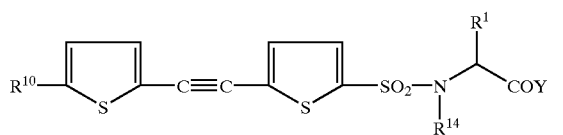

(XXII)

wherein $R^1$, $R^{10}$, $R^{14}$, and Y are as defined above, its optically active substance, their pharmaceutically acceptable salt, or hydrate thereof.

xxxi) A compound of the formula (XXIII):

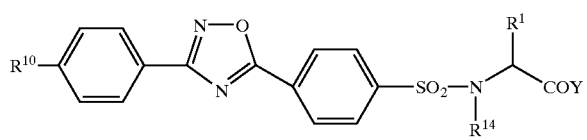

(XXIII)

wherein $R^1$, $R^{10}$, $R^{14}$ and Y are as defined above, its optically active substance, their pharmaceutically acceptable salt, or hydrate thereof.

xxxii) A pharmaceutical composition containing a compound of any one of above xxv) to xxxi).

xxxiii) A composition for inhibiting matrix metalloproteinase containing a compound of any one of above xxv) to xxxi).

xxxiv) A composition for inhibiting type IV collagenase containing a compound of any one of above xxv) to xxxi).

xxxv) A composition for treating or preventing glomerulopathy which contains a compound of any one of above xxv) to xxxi).

xxxvi) A composition for treating or preventing glomerulopathy which contains a compound of the formula (XXIV):

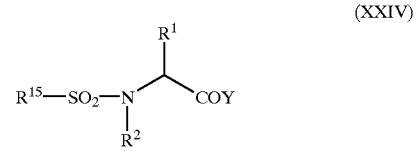

(XXIV)

wherein the combination of each substituent is represented below, its optically active substance, their pharmaceutically acceptable salt, or hydrate thereof.

TABLE 1

| Compound No. | Y | $R^1$ | $R^2$ | $R^{15}$ |
|---|---|---|---|---|
| 1 | NHOH | $(CH_3)_2CH-$ | H |  |
| 2 | NHOH | $(CH_3)_2CH-$ | Me |  |

TABLE 1-continued
| Compound No. | Y | R¹ | R² | R¹⁵ |
|---|---|---|---|---|
| 3 | OH | 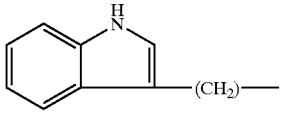 | H | 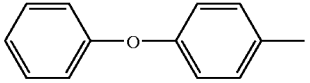 |
| 4 | NHOH | 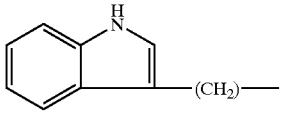 | H | 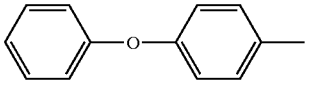 |
| 5 | OH | (CH₃)₂CH— | H | 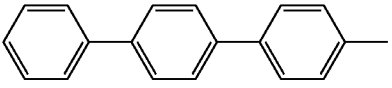 |
| 6 | OH | PhCH₂— | H | 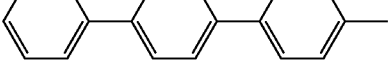 |
| 7 | OH | (CH₃)₂CH— | H | 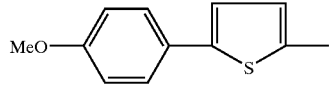 |
| 8 | OH | 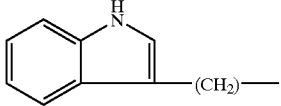 | H | 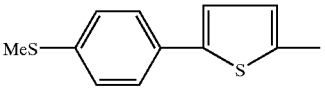 |
| 9 | NHOH | (CH₃)₂CH— | H | 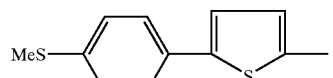 |
| 10 | OH | (CH₃)₂CH— | H | 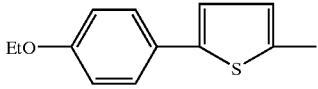 |
| 11 | OH | (CH₃)₂CH— | H | 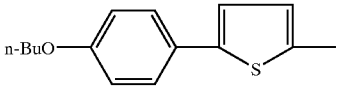 |
| 12 | OH | PhCH₂— | H | 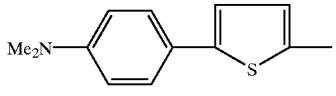 |
| 13 | OH | (CH₃)₂CH— | H | 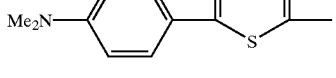 |
| 14 | OH | 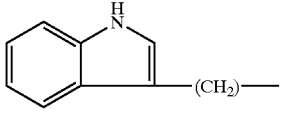 | H | 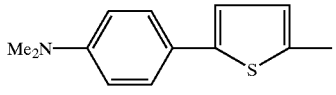 |
| 15 | OH | (CH₃)₂CH— | H | 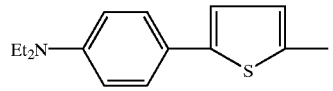 |

TABLE 1-continued

| Compound No. | Y | R¹ | R² | R¹⁵ |
|---|---|---|---|---|
| 16 | OH | (CH₃)₂CH— | H | 4-(N-methyl-N-ethylamino)phenyl-5-methylthiophen-2-yl |
| 17 | OH | PhCH₂— | H | 4-(N-methyl-N-ethylamino)phenyl-5-methylthiophen-2-yl |
| 18 | OH | PhCH₂— | H | 4-(diethylamino)phenyl-5-methylthiophen-2-yl |
| 19 | OH | CH₃— | H | 4-(dimethylamino)phenyl-5-methylthiophen-2-yl |
| 20 | OH | PhCH₂— | H | 4-aminophenyl-5-methylthiophen-2-yl |
| 21 | OH | PhCH₂— | H | 4-(methylamino)phenyl-5-methylthiophen-2-yl |
| 22 | OH | CH₃— | H | 4-(dimethylamino)phenyl-5-methylthiophen-2-yl |
| 23 | OH | PhCH₂— | H | 4-morpholinophenyl-5-methylthiophen-2-yl |
| 24 | OH | CH₃— | H | 4-(N-methyl-N-ethylamino)phenyl-5-methylthiophen-2-yl |
| 25 | OH | (CH₃)₂CH— | H | 4-aminophenyl-5-methylthiophen-2-yl |
| 26 | OH | (CH₃)₂CH— | H | 4-(hydroxymethyl)phenyl-5-methylthiophen-2-yl |
| 27 | OH | (CH₃)₂CH— | H | 4-(pyrrolidin-1-yl)phenyl-5-methylthiophen-2-yl |
| 28 | OH | H | H | 4-(dimethylamino)phenyl-5-methylthiophen-2-yl |
| 29 | OH | H | H | 4-(pyrrolidin-1-yl)phenyl-5-methylthiophen-2-yl |

TABLE 1-continued
| Compound No. | Y | R¹ | R² | R¹⁵ |
|---|---|---|---|---|
| 30 | OH | 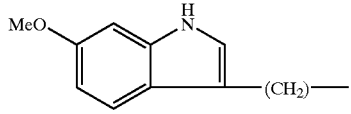 | H | 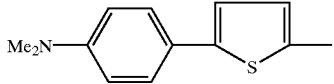 |
| 31 | OH | $(CH_3)_2CH-$ | H | 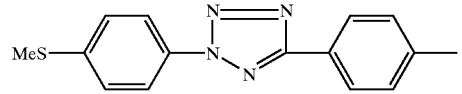 |
| 32 | OH | $PhCH_2-$ | H | 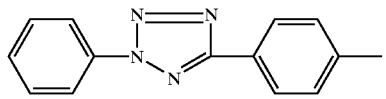 |
| 33 | NHOH | $PhCH_2-$ | H | 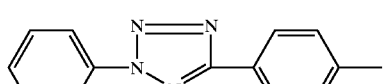 |
| 34 | OH | $PhCH_2-$ | H | 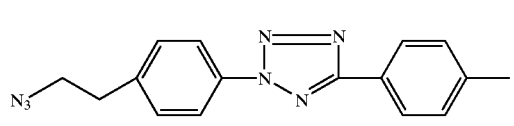 |
| 35 | OH | 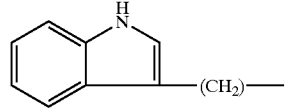 | H | 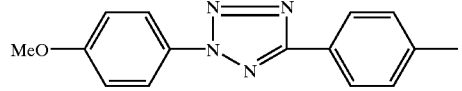 |
| 36 | OH | 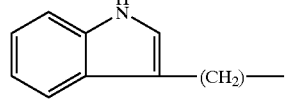 | H | 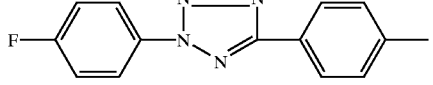 |
| 37 | OH |  | H | 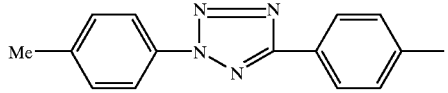 |
| 38 | OH | $(CH_3)_2CH-$ | H | 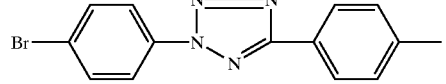 |
| 39 | OH | $(CH_3)_2CH-$ | H | 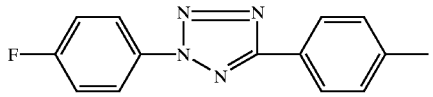 |
| 40 | OH |  | H | 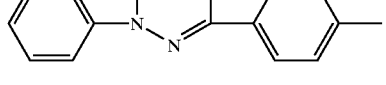 |
| 41 | OH | $PhCH_2-$ | H | 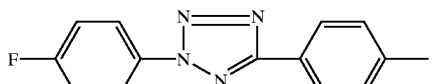 |
| 42 | NHOH | $(CH_3)_2CH-$ | H | 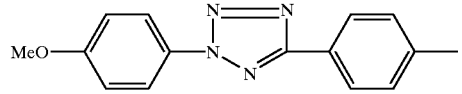 |

TABLE 1-continued

| Compound No. | Y | R¹ | R² | R¹⁵ |
|---|---|---|---|---|
| 43 | OH | PhCH₂— | H | 4-(HOCH₂CH₂)-C₆H₄-tetrazole-C₆H₄- |
| 44 | OH | PhCH₂— | H | 4-(N₃CH₂CH₂)-C₆H₄-tetrazole-C₆H₄- |
| 45 | OH | (CH₃)₂CH— | H | 4-Et-C₆H₄-tetrazole-C₆H₄- |
| 46 | OH | (CH₃)₂CH— | H | 4-Bu-C₆H₄-tetrazole-C₆H₄- |
| 47 | OH | (CH₃)₂CH— | H | 4-(HOCH₂CH₂)-C₆H₄-tetrazole-C₆H₄- |
| 48 | OH | PhNHCO(CH₂)₂— | H | 4-MeO-C₆H₄-tetrazole-C₆H₄- |
| 49 | OH | PhCH₂— | H | 4-Me-C₆H₄-tetrazole-C₆H₄- |
| 50 | OH | PhCH₂— | H | 4-MeO-C₆H₄-tetrazole-C₆H₄- |
| 51 | OH | (CH₃)₂CH— | H | 4-F₃C-C₆H₄-tetrazole-C₆H₄- |
| 52 | OH | (CH₃)₂CHCH₂— | H | 4-F-C₆H₄-tetrazole-C₆H₄- |
| 53 | OH | (CH₃)₂CH— | H | 4-NC-C₆H₄-tetrazole-C₆H₄- |
| 54 | OH | (CH₃)₂CH— | H | 4-BuO-C₆H₄-tetrazole-C₆H₄- |
| 55 | OH | (CH₃)₂CH— | H | 4-H₂NCO-C₆H₄-tetrazole-C₆H₄- |

TABLE 1-continued

| Compound No. | Y | R¹ | R² | R¹⁵ |
|---|---|---|---|---|
| 56 | OH | (CH₃)₂CH— | H | 4-acetylphenyl-tetrazole-4-methylphenyl |
| 57 | OH | CH₃— | H | 4-fluorophenyl-tetrazole-4-methylphenyl |
| 58 | OH | (CH₃)₂CH— | H | 4-acetamidophenyl-tetrazole-4-methylphenyl |
| 59 | OH | MeS—CH₂CH₂— | H | 4-fluorophenyl-tetrazole-4-methylphenyl |
| 60 | OH | 4-OH—Ph— | H | 4-fluorophenyl-tetrazole-4-methylphenyl |
| 61 | OH | PhCH₂— | H | 4-butoxyphenyl-tetrazole-4-methylphenyl |
| 62 | OH | PhCH₂— | H | 4-acetylphenyl-tetrazole-4-methylphenyl |
| 63 | OH | (CH₃)₂CH— | H | 4-methoxyphenyl-C≡C-thiophene-methyl |
| 64 | OH | (CH₃)₂CH— | H | 4-methylphenyl-C≡C-thiophene-methyl |
| 65 | NHOH | (CH₃)₂CH— | H | 4-methylphenyl-C≡C-thiophene-methyl |
| 66 | OH | PhCH₂— | H | 4-chlorophenyl-C≡C-thiophene-methyl |
| 67 | OH | PhCH₂— | H | 4-methoxyphenyl-C≡C-thiophene-methyl |
| 68 | OH | 1H-indol-3-yl-(CH₂)— | H | 4-methylphenyl-C≡C-thiophene-methyl |

TABLE 1-continued
| Compound No. | Y | R¹ | R² | R¹⁵ |
|---|---|---|---|---|
| 69 | OH | 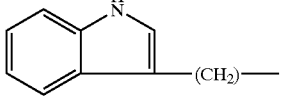 | H | 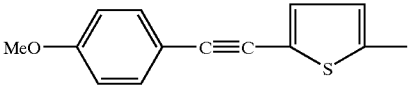 |
| 70 | NHOH | 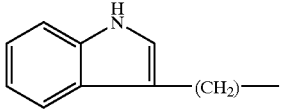 | H | 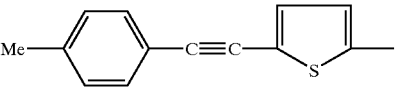 |
| 71 | NHOH | (CH₃)₂CH— | H | 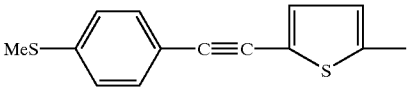 |
| 72 | NHOH | 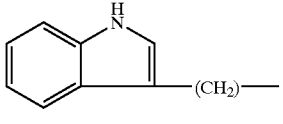 | H | 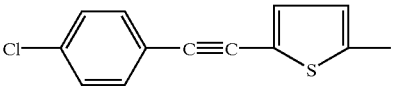 |
| 73 | OH | 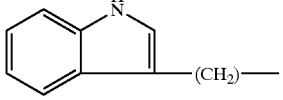 | H | 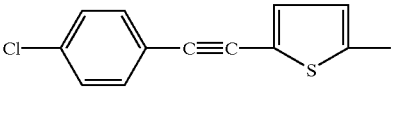 |
| 74 | OH | (CH₃)₂CH— | H | 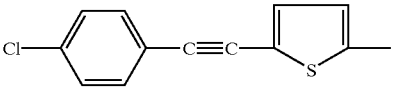 |
| 75 | OH | (CH₃)₂CH— | H | 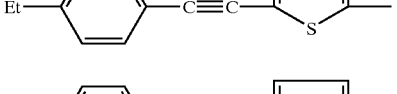 |
| 76 | OH |  | H | 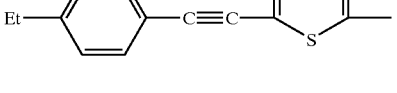 |
| 77 | OH | PhCH₂— | H | 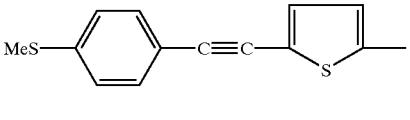 |
| 78 | OH | 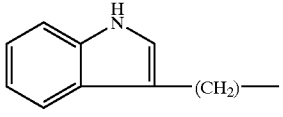 | H |  |
| 79 | OH | (CH₃)₂CH— | H | 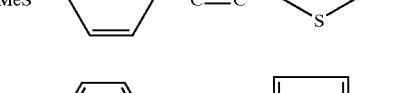 |
| 80 | NHOH | 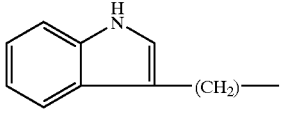 | H | 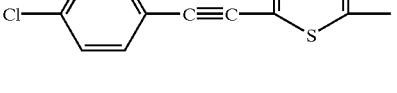 |

TABLE 1-continued

| Compound No. | Y | R¹ | R² | R¹⁵ |
|---|---|---|---|---|
| 81 | OH | indol-3-yl-(CH₂)– | H | 4-(HOH₂C)C₆H₄–C≡C–(5-methylthiophen-2-yl) |
| 82 | OH | indol-3-yl-(CH₂)– | H | 4-(Me₂N(CH₂)₃O)C₆H₄–C≡C–(5-methylthiophen-2-yl) |
| 83 | OH | indol-3-yl-(CH₂)– | H | 4-(HOCH₂CH₂)C₆H₄–C≡C–(5-methylthiophen-2-yl) |
| 84 | OH | (CH₃)₂CH– | H | 4-(HOCH₂CH₂)C₆H₄–C≡C–(5-methylthiophen-2-yl) |
| 85 | OH | PhCH₂– | H | 4-(HOCH₂CH₂)C₆H₄–C≡C–(5-methylthiophen-2-yl) |
| 86 | OH | indol-3-yl-(CH₂)– | H | 4-(morpholino)C₆H₄–C≡C–(5-methylthiophen-2-yl) |
| 87 | OH | PhCH₂– | H | (5-methylthiophen-2-yl)–C≡C–(5-methylthiophen-2-yl) |
| 88 | OH | indol-3-yl-(CH₂)– | H | 4-Me-C₆H₄–C≡C–C₆H₄-4- |
| 89 | NHOH | indol-3-yl-(CH₂)– | H | 4-MeO-C₆H₄–C≡C–C₆H₄-4- |
| 90 | OH | indol-3-yl-(CH₂)– | H | 4-Br-C₆H₄–C(O)NH–C₆H₄-4- |
| 91 | OH | indol-3-yl-(CH₂)– | H | 4-O₂N-C₆H₄–C(O)NH–C₆H₄-4- |
| 92 | OH | indol-3-yl-(CH₂)– | H | 4-F-C₆H₄–C(O)NH–C₆H₄-4- |

TABLE 1-continued

| Compound No. | Y | R¹ | R² | R¹⁵ |
|---|---|---|---|---|
| 93 | OH | PhCH₂— | H | 4-Me-C₆H₄-C(O)-NH-C₆H₄-4- |
| 94 | OH | PhCH₂— | H | 4-MeS-C₆H₄-C(O)-NH-C₆H₄-4- |
| 95 | OH | PhCH₂— | H | 4-Me-C₆H₄-tetrazolyl-thienyl- |
| 96 | OH | (CH₃)₂CH— | H | 4-Me-C₆H₄-tetrazolyl-thienyl- |
| 97 | OH | (CH₃)₂CH— | H | 4-F-C₆H₄-tetrazolyl-thienyl- |
| 98 | OH | (CH₃)₂CH— | H | phenyl-oxazolyl-thienyl- |
| 99 | OH | (CH₃)₂CH— | H | 4-Me-C₆H₄-dioxadiazolyl-C₆H₄-4- |
| 100 | OH | (CH₃)₂CH— | H | 4-(Et₂N)-biphenyl- |
| 101 | OH | (CH₃)₂CH— | H | 4-(MeEtN)-biphenyl- |
| 102 | OH | (CH₃)₂CH— | H | 4-(Me₂N)-biphenyl- |
| 103 | OH | (CH₃)₂CH— | H | 4-Me-C₆H₄-thienyl-C₆H₄-4- |
| 104 | OH | (CH₃)₂CH— | H | 4-F₃C-C₆H₄-tetrazolyl-C₆H₄-4- |
| 105 | OH | PhCH₂— | H | 4-F-C₆H₄-tetrazolyl-C₆H₄-4- |

TABLE 1-continued

| Compound No. | Y | R¹ | R² | R¹⁵ |
|---|---|---|---|---|
| 106 | OH | (CH₃)₂CH— | H | 4-F-C₆H₄-tetrazole-N-C₆H₄- (4-F-phenyl tetrazolyl-phenyl) |
| 107 | OH | (CH₃)₂CH— | H | 4-Et-C₆H₄-tetrazole-N-C₆H₄- |
| 108 | OH | PhCH₂— | H | 4-Et-C₆H₄-tetrazole-N-C₆H₄- |
| 109 | OH | 1H-indol-3-yl-(CH₂)— | H | 4-Et-C₆H₄-tetrazole-N-C₆H₄- |
| 110 | OH | PhCH₂— | H | 4-Et-C₆H₄-tetrazole-N-C₆H₄- |
| 111 | OH | 1H-indol-3-yl-(CH₂)— | H | 4-F-C₆H₄-tetrazole-N-C₆H₄- |
| 112 | OH | (CH₃)₂CH— | H | 4-Et-C₆H₄-tetrazole-N-C₆H₄- |
| 113 | OH | (CH₃)₂CHCH₂— | H | 4-Et-C₆H₄-tetrazole-N-C₆H₄- |
| 114 | OH | CH₃— | H | 4-F-C₆H₄-tetrazole-N-C₆H₄- |
| 115 | OH | PhCH₂— | H | Ph-tetrazole-N-C₆H₄- |
| 116 | OH | H | H | 4-Et-C₆H₄-tetrazole-N-C₆H₄- |
| 117 | OH | CH₃— | H | 4-Et-C₆H₄-tetrazole-N-C₆H₄- |
| 118 | OH | (CH₃)₂CH— | H | 4-EtO-C₆H₄-tetrazole-N-C₆H₄- |

TABLE 1-continued

| Compound No. | Y | R¹ | R² | R¹⁵ |
|---|---|---|---|---|
| 119 | OH | (CH₃)₂CH— | H | Me₂N-C₆H₄-tetrazole-C₆H₄- |
| 120 | OH | (CH₃)₂CH— | H | MeS-C₆H₄-tetrazole-C₆H₄- |
| 121 | OH | (CH₃)₂CH— | H | n-Bu-C₆H₄-tetrazole-C₆H₄- | xxxvii) A composition for treating or preventing glomerulopathy which contains a compound of the formula (XXIV):

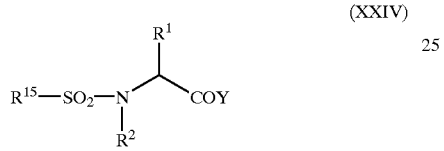
(XXIV)

wherein the combination of each substituent is represented below, its optically active substance, their pharmaceutically acceptable salt, or hydrate thereof

TABLE 2

| Compound No. | Y | R¹ | R² | R¹⁵ |
|---|---|---|---|---|
| 1 | NHOH | (CH₃)₂CH— | H | Ph-O-C₆H₄- |
| 2 | NHOH | (CH₃)₂CH— | Me | Ph-O-C₆H₄- |
| 3 | OH | indol-3-yl-(CH₂)— | H | Ph-O-C₆H₄- |
| 4 | NHOH | indol-3-yl-(CH₂)— | H | Ph-O-C₆H₄- |
| 5 | OH | (CH₃)₂CH— | H | biphenyl-C₆H₄- (terphenyl) |
| 6 | OH | PhCH₂— | H | biphenyl-C₆H₄- (terphenyl) |

TABLE 2-continued

| Compound No. | Y | R¹ | R² | R¹⁵ |
|---|---|---|---|---|
| 7 | OH | (CH₃)₂CH— | H | MeO-C₆H₄-(5-methylthiophen-2-yl) |
| 31 | OH | (CH₃)₂CH— | H | MeO-C₆H₄-N(tetrazole)-C₆H₄-Me |
| 32 | OH | PhCH₂— | H | Ph-N(tetrazole)-C₆H₄-Me |
| 33 | NHOH | PhCH₂— | H | Ph-N(tetrazole)-C₆H₄-Me |
| 34 | OH | PhCH₂— | H | N₃-CH₂CH₂-C₆H₄-N(tetrazole)-C₆H₄-Me |
| 35 | OH | indol-3-yl-(CH₂)— | H | MeO-C₆H₄-N(tetrazole)-C₆H₄-Me |
| 36 | OH | indol-3-yl-(CH₂)— | H | F-C₆H₄-(tetrazole)-N-C₆H₄-Me |
| 37 | OH | indol-3-yl-(CH₂)— | H | Me-C₆H₄-N(tetrazole)-C₆H₄-Me |
| 38 | OH | (CH₃)₂CH— | H | Br-C₆H₄-N(tetrazole)-C₆H₄-Me |
| 39 | OH | (CH₃)₂CH— | H | F-C₆H₄-(tetrazole)-N-C₆H₄-Me |
| 63 | OH | (CH₃)₂CH— | H | MeO-C₆H₄-C≡C-(5-methylthiophen-2-yl) |
| 64 | OH | (CH₃)₂CH— | H | Me-C₆H₄-C≡C-(5-methylthiophen-2-yl) |
| 65 | NHOH | (CH₃)₂CH— | H | Me-C₆H₄-C≡C-(5-methylthiophen-2-yl) |

TABLE 2-continued
| Compound No. | Y | R¹ | R² | R¹⁵ |
|---|---|---|---|---|
| 66 | OH | PhCH₂— | H | 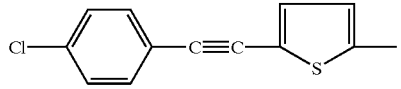 |
| 67 | OH | PhCH₂— | H | 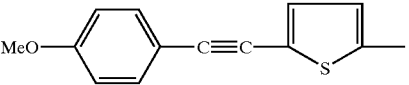 |
| 68 | OH | 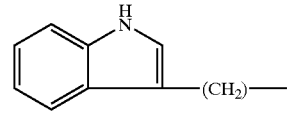 | H | 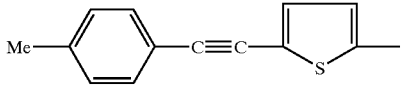 |
| 69 | OH | 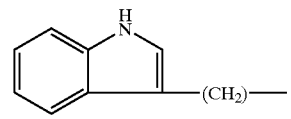 | H | 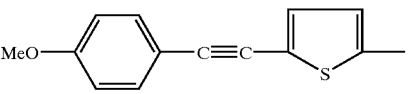 |
| 70 | NHOH | 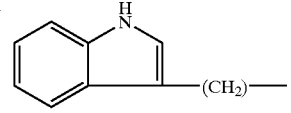 | H | 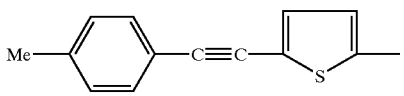 |
| 71 | NHOH | (CH₃)₂CH— | H | 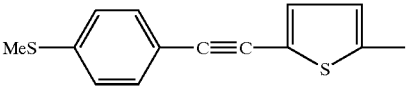 |
| 72 | NHOH | 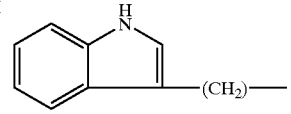 | H | 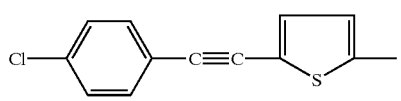 |
| 88 | OH | 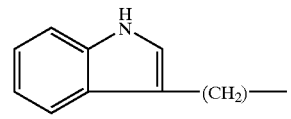 | H | 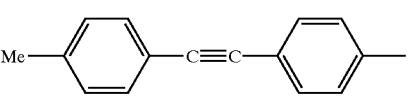 |
| 89 | NHOH | 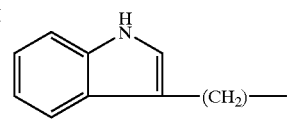 | H | 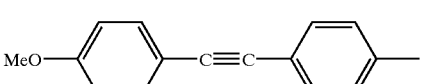 |
| 90 | OH | 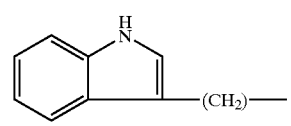 | H | 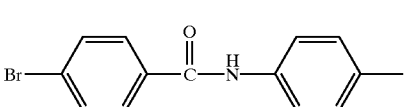 |
| 91 | OH | 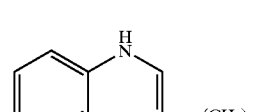 | H | 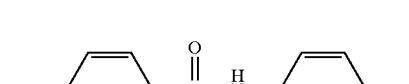 |
| 92 | OH | 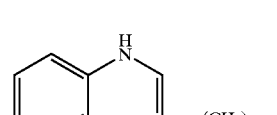 | H | 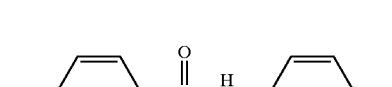 |

TABLE 2-continued

| Compound No. | Y | R¹ | R² | R¹⁵ |
|---|---|---|---|---|
| 93 | OH | PhCH₂— | H | Me—C₆H₄—C(=O)—NH—C₆H₄— |
| 94 | OH | PhCH₂— | H | MeS—C₆H₄—C(=O)—NH—C₆H₄— | xxxviii) The composition for treating or preventing glomerulopathy of any one of above xxxv) to xxxvii), wherein glomerulopathy is glomerulonephritis.

xxxix) The composition for treating or preventing glomerulopathy of any one of above xxxv) to xxxvii), wherein glomerulopathy is diabetic nephropathy.

Among the above mentioned compounds with superior activity for treating or preventing glomerulopathy, preferred are shown below.

Compound No.: 1, 2, 3, 4, 5, 6, 7, 8, 9, 10, 11, 12, 13, 15, 16, 17, 18, 19, 20, 21, 23, 24, 26, 28, 29, 31, 32, 33, 34, 35, 39, 40, 41, 44, 48, 51, 52, 54, 55, 56, 57, 59, 61, 62, 73, 81, 82, 84, 86, 91, 92, 93, 94, 95, 97, 98, 100, 101, 102, 103, 104, 105, 106, 107, 108, 109, 112, 113, 114, 115, 119, 120, and 121.

More preferred compounds are No.: 1, 2, 3, 4, 5, 6, 7, 9, 12, 13, 15, 16, 17, 18, 19, 22, 29, 31, 32, 33, 34, 35, 39, 51, 54, 55, 56, 57, 59, 61, 62, 80, 82, 84, 86, 91, 92, 92, 94, 95, 96, 97, 101, 108, 112, 113, 115, 119, 120, and 121.

Most preferred compounds are No.: 1, 2, 4, 7, 9, 12, 15, 16, 17, 18, 19, 23, 31, 33, 32, 34, 39, 54, 56, 57, 61, 62, 80, 84, 86, 91, 92, 95, 97, 101, 108, and 121.

The term "glomerulopathy" herein used means dysfunction of glomerulus or change of form of glomerulus caused by an endogenous or exogenous factor.

The term "glomerulonephritis" herein used means renal dysfunction derived from glomerulus dysfunction which is caused by a hereditary or exogenous factor or autoimmune disorder. This term includes nephrosis such as membranous nephropathy without inflammatory response.

The term "diabetic nephropathy" herein used means all renal dysfunction observed after crisis of diabetes.

The term "lower alkyl" herein used means $C_1$ to $C_6$ straight or branched chain alkyl, for example, methyl, ethyl, n-propyl, i-propyl, n-butyl, i-butyl, sec-butyl, tert-butyl, n-pentyl, n-hexyl, and the like. $C_1$ to $C_4$ alkyl is preferred.

The term "cycloalkyl" herein used are exemplified by cyclopropyl, cyclobutyl, cyclopentyl, cyclohexyl, cycloheptyl, and the like.

The term "aryl" herein used means monocyclic or condensed ring aromatic hydrocarbons. Examples of the aryl are phenyl, 1-naphthyl, 2-naphthyl, and the like.

The term "aralkyl" herein used means the above mentioned "lower alkyl" substituted with the above mentioned "aryl" at any possible position. Examples of the aralkyl are benzyl, phenethyl (2-phenethyl), phenylpropyl (e.g., 3-phenylpropyl), naphthylmethyl (e.g., 1-naphthylmethyl and 2-naphthylmethyl), anthrylmethyl (e.g., 9-anthrylmethyl), and the like. Benzyl is preferred.

The term "heteroaryl" herein used means a 5 to 6 membered aromatic heterocyclic group which contains one or more hetero atoms selected from the group consisting of oxygen, sulfur, and nitrogen atoms in the ring and may be fused with the above mentioned "aryl", "non-aromatic heterocyclic group", and other "heteroaryl" at any possible position. Examples of the heteroaryl are pyrrolyl (e.g., 1-pyrrolyl), indolyl (e.g., 3-indolyl), carbazolyl (e.g., 3-carbazolyl), imidazolyl (e.g., 4-imidazolyl), pyrazolyl (e.g., 1-pyrazolyl), benzimidazolyl (e.g., 2-benzimidazolyl), indazolyl (e.g., 3-indazolyl), indolizinyl (e.g., 6-indolizinyl), pyridyl (e.g., 4-pyridyl), quinolyl (e.g., 5-quinolyl), isoquinolyl (e.g., 3-isoquinolyl), acridinyl (e.g., 1-acridinyl), phenanthridinyl (e.g., 2-phenanthridinyl), pyridazinyl (e.g., 3-pyridazinyl), pyrimidinyl (e.g., 4-pyrimidinyl), pyrazinyl (e.g., 2-pyrazinyl), cinnolinyl (e.g., 3-cinnolinyl), phthalazinyl (e.g., 2-phthalazinyl), quinazolinyl (e.g., 2-quinazolinyl), isooxazolyl (e.g., 3-isooxazolyl), benzisoxazolyl (e.g., 3-benzisoxazolyl), oxazolyl (e.g., 2-oxazolyl), benzoxazolyl (e.g., 2-benzoxazolyl), benzoxadiazolyl (e.g., 4-benzoxadiazolyl), isothiazolyl (e.g., 3-isothiazolyl), benzisothiazolyl (e.g., 2-benzisothiazolyl), thiazolyl (e.g., 2-thiazolyl), benzothiazolyl (e.g., 2-benzothiazolyl), furyl (e.g., 3-furyl), benzofuryl (e.g., 3-benzofuryl), thienyl (e.g., 2-thienyl), benzothienyl (e.g., 2-benzothienyl), tetrazolyl, and the like. Indolyl, pyrazolyl, and pyridyl are preferred.

The term "heteroarylalkyl" herein used means the above mentioned "lower alkyl" substituted with the above mentioned "heteroaryl" at any possible position. Examples of the heteroarylalkyl are thiazolylmethyl (e.g., 4-thiazolylmethyl), thiazolylethyl (e.g., 5-thiazolyl-2-ethyl), indolylmethyl (e.g., indol-3-ylmethyl), imidazolylmethyl (e.g., 4-imidazolylmethyl), benzothiazolylmethyl (e.g., 2-benzothiazolylmethyl), benzopyrazolylmethyl (e.g., 1-benzopyrazolylmethyl), benzotriazolylmethyl (e.g., 4-benzotriazolylmethyl), benzoquinolylmethyl (e.g., 2-benzoquinolylmethyl), benzimidazolylmethyl (e.g., 2-benzimidazolylmethyl), pyridylmethyl (e.g., 2-pyridylmethyl), and the like. As a preferred heteroarylalkyl, indol-3-ylmethyl is exemplified.

The term "non-aromatic heterocyclic group" herein used means a 5 to 7 membered non-aromatic ring which contains one or more hetero atoms selected from the group consisting of oxygen, sulfur, and nitrogen atoms in the ring and condensed ring which are fused with two or more themselves. Examples of the non-aromatic heterocyclic group are pyrrolidine, piperidine, piperazine, octahydroquinoline, tetrahydrofuran, tetrahydropyrane, morpholine, and the like. Pyrrolidine and morpholine are preferred.

The term "lower alkyloxy" herein used means alkyloxy of which alkyl part is the above mentioned lower alkyl. Examples of the lower alkyloxy are methyloxy, ethyloxy, n-propyloxy, i-propyloxy, n-butyloxy, i-butyloxy, sec-butyloxy, tert-butyloxy, and the like. C1 to C4 alkyloxy is preferred.

The term "halogen" herein used means fluoro, chloro, bromo, and iodo. Fluoro, chloro, and bromo are preferred.

The term "lower alkylthio" herein used means alkylthio of which alkyl part is the above mentioned "lower alkyl". Examples of the lower alkylthio are methylthio, ethylthio, and the like.

The term "lower alkyloxycarbonyl" herein used means lower alkyloxycarbonyl of which alkyloxy part is the above mentioned "lower alkyloxy". Examples of the lower alkyloxycarbonyl are methyloxycarbonyl, ethyloxycarbonyl, n-propyloxycarbonyl, and the like.

The term "lower haloalkyl" herein used means the above mentioned "lower alkyl" which is substituted with the above mentioned "halogen" at 1 to 5 positions. Examples of the lower haloalkyl are trichloromethyl, trichloroethyl, trifluoromethyl, trifluoroethyl, and the like.

The term "aryloxy" herein used means aryloxy of which aryl part is the above mentioned "aryl". Examples of the aryloxy are phenyloxy and the like.

The term "lower alkenyl" herein used means $C_2$ to $C_6$ straight or branched chain alkenyl. Examples of the lower alkenyl are vinyl, allyl, propenyl, butenyl, and the like.

The term "lower alkynyl" herein used means $C_2$ to $C_8$ straight or branched chain alkynyl. Examples of the lower alkynyl are ethynyl, 1-propynyl, propargyl, 1-hexynyl, and the like.

The term "acyl" herein used means alkanoyl of which carbonyl is bonded to the above mentioned "lower alkyl" or "cycloalkyl" and aroyl of which carbonyl is bonded to the above mentioned "aryl". Examples of the acyl are acetyl, n-propanoyl, isopropanoyl, n-butyloyl, t-butyloyl, cyclopropanoyl, cyclobutanoyl, cyclopentanoyl, cyclohexanoyl, benzoyl, and the like. Acetyl and benzoyl are preferred.

The term "alkanoyl" herein used means alkanoyl of which carbonyl is bonded to the above mentioned "lower alkyl" or "cycloalkyl". Examples of the alkanoyl are acetyl, n-propanoyl, isopropanoyl, n-butyloyl, t-butyloyl, cyclopropanoyl, cyclobutanoyl, cyclopentanoyl, cyclohexanoyl, and the like. Acetyl is preferred.

The term "acyloxy" herein used means acyloxy of which oxygen atom is bonded directly to the above mentioned "acyl". Examples of the acyloxy are acetyloxy, n-propanoyloxy, isopropanoyloxy, n-butyloyloxy, t-butyloyloxy, cyclopropanoyloxy, cyclobutanoyloxy, cyclopentanoyloxy, cyclohexanoyloxy, benzoyloxy, α-naphthoyloxy, β-naphthoyloxy, and the like.

The term "optionally substituted amino" herein used means amino substituted with one, two, or more of the above mentioned "lower alkyl", "aralkyl", or "heteroarylalkyl" or non-substituted. Examples of the optionally substituted amino are amino, methylamino, dimethylamino, ethylmethylamino, diethylamino, benzylamino, and the like.

The substituents of "optionally substituted alkyl" for $R^1$ and $R^2$ are hydroxy, alkyloxy (e.g., methyloxy and ethyloxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, lower alkyloxycarbonyl (e.g., methyloxycarbonyl and ethyloxycarbonyl), nitro, cyano, lower haloalkyl (e.g., trifluoromethyl), optionally substituted amino (e.g., methylamino, dimethylamino, and carbamoylamino), optionally substituted carbamoyl (e.g., phenylcarbamoyl), guanidino, phenyl, benzyloxy, and the like. These substituents are able to bind to it at one or more of any possible positions.

Examples of "optionally substituted alkyl" of $R^1$ and $R^2$ are methyl, ethyl, n-propyl, i-propyl, i-butyl, phenylcarbamoylethyl, methylthioethyl, and the like.

The substituents for "optionally substituted alkyl" of $R^5$, $R^6$, $R^{12}$, and $R^{13}$ are optionally protected hydroxy (e.g., hydroxy, methylsulfonyloxy, and p-toluenesulfonyloxy), alkyloxy (e.g., methyloxy, ethyloxy, n-propyloxy, and u-butyloxy), azide, mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, lower alkyloxycarbonyl (e.g., methyloxycarbonyl and ethyloxycarbonyl), nitro, cyano, lower haloalkyl (e.g., trifluoromethyl), optionally substituted amino (e.g., methylamino, dimethylamino, and carbamoylamino), guanidino, phenyl, benzyloxy, and the like. These substituents are able to bind to it at one or more of any possible positions. Preferred substituents are optionally protected hydroxy, azide, halogen, and optionally substituted amino.

Examples of "optionally substituted alkyl" of $R^5$, $R^6$, $R^{12}$, and $R^{13}$ are methyl, ethyl, n-propyl, i-propyl, n-butyl, hydroxymethyl, 2-hydroxyethyl, 2-ehtylazide, trifluoromethyl, and the like.

The substituents for "optionally substituted alkyl" of $R^8$, $R^9$, $R^{12}$, and $R^{13}$ are optionally protected hydroxy (e.g., hydroxy, methylsulfonyloxy, and p-toluenesulfonyloxy), alkyloxy (e.g., methyloxy and ethyloxy), azide, mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, lower alkyloxycarbonyl (e.g., methyloxycarbonyl and ethyloxycarbonyl), nitro, cyano, lower haloalkyl (e.g., trifluoromethyl), optionally substituted amino (e.g., methylamino, dimethylamino, and carbamoylamino), guanidino, phenyl, benzyloxy, and the like. These substituents are able to bind to it at one or more of any possible positions. Preferred substituents are optionally protected hydroxy, azide, halogen, and optionally substituted amino.

Examples of the substituents of "optionally substituted alkyloxy" herein used are optionally substituted amino (amino, methylamino, dimethylamino, ethylamino, ethylmethylamino, and diethylamino), and the like. Preferred is optionally substituted amino.

Examples of "optionally substituted alkyloxy" are methyloxy, ethyloxy, n-propyloxy, n-butyloxy, 3-dimethylaminopropyloxy, and the like.

Substituents on the aromatic ring of "optionally substituted aryl", "optionally substituted aralkyl", "optionally substituted heteroaryl", and "optionally substituted heteroarylalkyl" are, for example, hydroxy, lower alkoxy (e.g., methyloxy and ethyloxy), mercapto, lower alkylthio (e.g., methylthio), cycloalkyl (e.g., cyclopropyl, cyclobutyl, and cyclopentyl), halogen (e.g., fluoro, chloro, bromo, and iodo), carboxy, lower alkyloxycarbonyl (e.g., methyloxycarbonyl and ethyloxycarbonyl), nitro, cyano, lower haloalkyl (e.g., trifluoromethyl), aryloxy (e.g., phenyloxy), optionally substituted amino (e.g., methylamino, dimethylamino, diethylamino, and benzylidenamino), guanidino, lower alkyl (e.g., methyl, ethyl, n-propyl, i-propyl, n-butyl, i-butyl, sec-butyl, tert-butyl, n-pentyl, i-pentyl, neo-pentyl, and tert-pentyl), lower alkenyl (e.g., vinyl and propenyl), alkynyl (e.g., ethynyl and phenylethynyl), lower alkanoyl (e.g., formyl, acetyl, and propionyl), acyloxy (e.g., acetyloxy), acylamino, lower alkylsulfonyl (e.g., methylsulfonyl), phenyl, benzyl, an azo group (e.g., phenylazo), optionally substituted heteroaryl (e.g., 3-pyridyl), optionally substituted ureido (e.g., ureido and phenylureido), and the like. These substituents are able to bind to it at one or more of any possible positions.

The examples of the substituents for "optionally substituted non-aromatic heterocyclic group" are lower alkyl (e.g., methyl, ethyl, n-propyl, and i-propyl) and the like.

The examples of "optionally substituted non-aromatic heterocyclic group" are 1-pyrrolidinyl, morpholino, piperidino, oxazolidino, and the like.

BEST MODE FOR CARRYING OUT THE INVENTION

Figure 1:
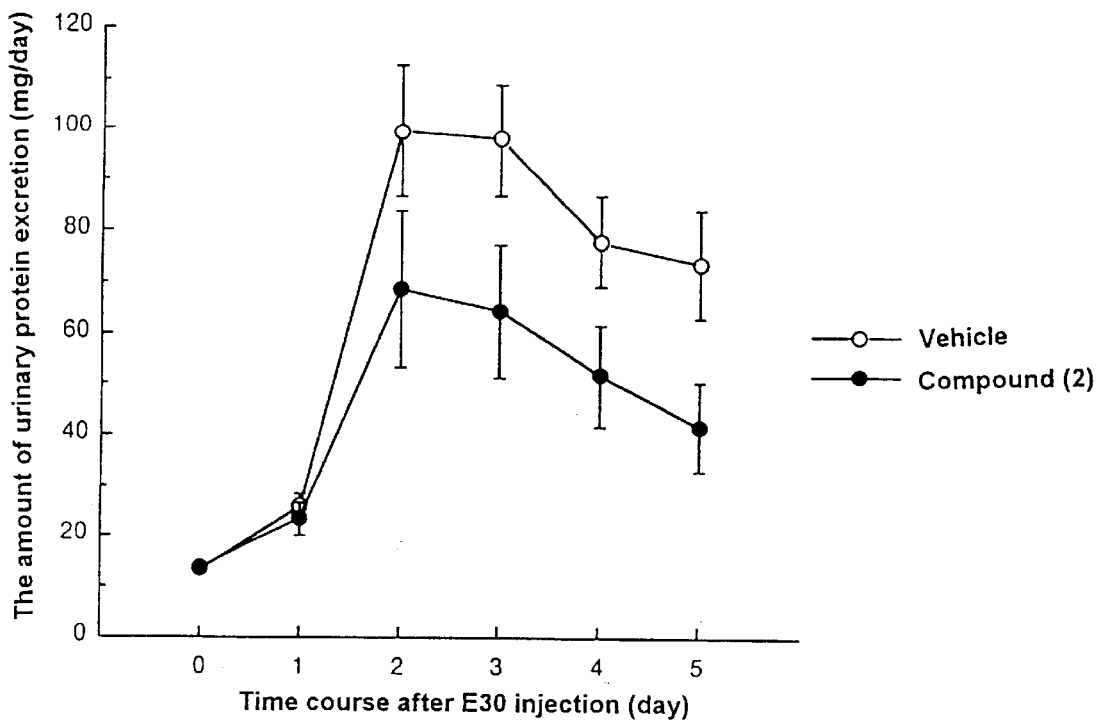
FIG. 1 shows changes in the amount of urinary protein excretion with time course after E30 injection.

The effect as a treating or preventing agent is tested below.
(Animals)

Five to eight weeks old male Slc-Wistar rats were used in the experiment.
(Procedure for the Establishment of Nephritogenic Antibody)

Mouse monoclonal antibodies are established against rat glomeruli and the monoclonal antibodies which induced nephritis are screened as described below.

To induce glomerulonephritis by the injection of antibody, the presence of the antigen on the cell surface is required. First of all, we investigated by immunofluorescence whether or not obtained monoclonal antibodies accumulate in the glomeruli after the intravenous injection to rats. The antigen recognized each clone of monoclonal antibodies was defined its distribution and molecular weight. Furthermore, nephritis-inducing activity was evaluated based on the urinary excretion of protein within a week after single injection of antibody.

During this study, a monoclonal antibody E30 was established (J.J.N., vol. 36, p106, 1994). It has been known that E30 recognizes the surface antigen of mesangial cells by the immunohistochemical study, and that single administration of E30 to rats induces complement-dependent mesangial cell injury. The pathological changes are described below.

E30 antibodies immediately bind to the surface antigens of mesangial cells in glomeruli after a intravenous injection to rats, followed by the activation of compliment system within 30 min. And then, degeneration and necrosis of mesangial cells are occurred, resulting in the detachment of glomerular basement membrane from mesangial area. A series of these pathological features is known as mesangiolysis. Accumulation of platelet and infiltration of inflammatory cells such as polymorphonuclear leukocyte and macrophage are observed during mesangiolysis. Mesangiolysis is prominent 1–3 days after the injection of the antibody and mesangial expansion is frequently observed at that time. Proliferation of glomerular cells, mainly mesangial cells, is initiated 3–5 days after the injection, resulting in the morphological features of mesangial proliferative glomerulonephritis by a week. The reconstruction of the glomerular capillary network is accompanied with mitosis and proliferation of mesangial cells and irregular patterns of angiogenesis. After then, increased number of mesangial cells and overproduced extracellular matrix are resolved with time course and the pathological features recover to the normal one by a month.

Thus, since a single injection of the monoclonal antibody induces a reproducible nephritis model, the antibody-induced nephritis model is useful for grasping a basic changes in glomerular disease as a biological response.

In Asia, a half of the patients with glomerulonephritis was diagnosed as IgA nephropathy. IgA nephropathy is characterized as IgA deposition to glomerular mesangial cells. IgA nephropathy belongs to proliferative nephritis caused by immunoreaction against mesangial cell itself Therefore, the monoclonal antibody-induced nephritis model is also useful for studying the pathogenesis of IgA nephropathy.

In addition, the monoclonal antibody, E30, is available for establishing some chronic nephritis models induced by the combination dosing with puromycin aminonucleoside (J.J.N., vol. 39, p220, 1997) or by a single injection of it to uni-nephrectomized rats (J.J.N., vol. 39, p300, 1997). The preventing or treating effects of test compounds on the development of glomerulosclerosis could be evaluated by utilizing these chronic nephritis models. Similar experiments can be examined by using following methods: 1) methods by using other monoclonal antibodies or anti-thymocyte serum instead of E30, 2) methods by using hereditary nephrosis rats or mice, 3) methods by using spontaneously diabetic rats or mice, and 4) methods by using streptozotocin- or alloxan-induced diabetic rats or mice.
(Protocol for Assay)

In order to induce glomerulonephritis, E30 of 20 to 500 μg, preferably 50 to 200 μg, is intravenously injected to rats of five to eight weeks old. Test compounds of 0.1 to 500 mg, preferably 1 to 200 mg, are suspended with 3 to 10%, preferably 4 to 6%, gum arabic solution and the like, and are orally given 1 to 5 hours, preferably 1.5 to 3 hours, prior to E30 injection. Constant amount of test compounds are then consecutively given 1 to 3 times a day. Evaluation of test compounds are determined by the amount of urinary protein excretion 2 days after E30 injection when proteinuria reaches to the maximum level.

As for some compounds which exhibit antiproteinuric effects in the method described above, the amount of urinary protein excretion during 5 to 8 days, changes in body weight, morphological changes in glomeruli by autopsy, inhibitory ratio of mesangial proliferation and renal function are assessed after the treatment of these compounds.

Determination of the amount of urinary protein excretion is performed by the collection of 24-hour urine samples with stainless metabolic cages followed by the measurement of the concentration of urinary protein. Blood samples obtained at the follow-up period are processed for the determination of blood urea nitrogen and plasma creatinine, which indicate renal function. As a marker of damaged renal tubules, urinary amounts of N-acetyl-D-glycosaminidase excretion is measured. Furthermore, to study the inhibitory effects of compounds on mesangial proliferation following E30 injection, the number of PCNA (proliferating cell nuclear antigen) positive cells per single glomerulus is counted. Morphological changes are observed with light and electron microscopy.

The present compound represented by the formula (I) which useful as the composition for treating or preventing glomerulopathy is may be synthesized in accordance with the method described in WO97/27174.

The term "compound of the present invention" herein used includes pharmaceutically acceptable salt or hydrate of the compound. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, mallein acid, fumaric acid, benzenesulfonic acid, p-toluenesulfonic acid, and the like). These salts can be formed by the usual method.

When the compound of the present invention is administered to a person for the treatment or prevention of the above diseases, they can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the daily dosage can generally be between 0.1 to 100 mg/kg/day, preferably 1 to 20 mg/kg/day for adult.

The following examples are provided to further illustrate the present invention and are not to be constructed as limiting the scope thereof.

Abbreviations described below are used in the following examples.
Me: methyl
tBu: tert-butyl
DMSO: dimethylsulfoxide
p-TsOH: p-toluenesulfonic acid
(The Preparation of the Compound)

EXAMPLE 1

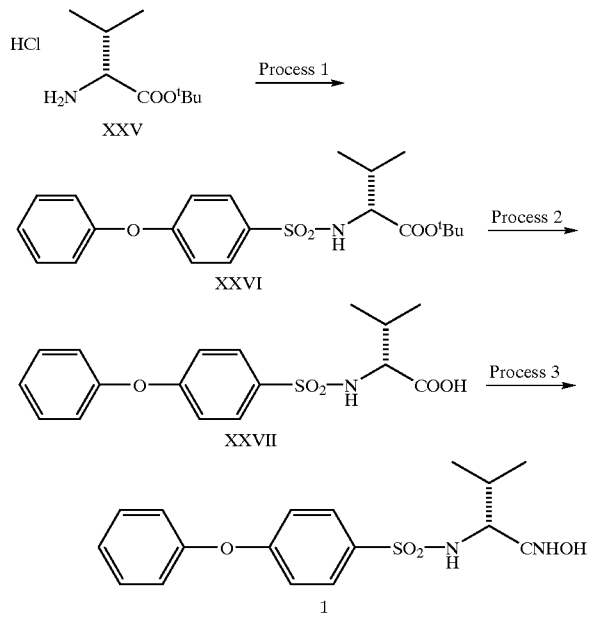

Process 1

To a solution of 4.72 g (22.5 mmol) of D-valine tert-butyl ester hydrochloride (XXV) in dichloromethane (100 ml) were added 6.19 ml (2.5×22.5 mmol) of N-methylmorpholine and 6.37 g (1.05×22.5 mmol) of 4-phenoxybenzenesulfonyl chloride under ice-cooling. After the mixture was stirred for 5 h at room temperature, the reaction mixture was diluted with ethyl acetate. The organic layer was washed with 1N-hydrochloric acid and saturated sodium hydrogencarbonate aq., dried over sodium sulphate, and concentrated in vacuo. The residue was subjected to silica gel column chromatography and the fraction eluting with $CHCl_3/MeOH=50/1$ was collected, recrystallized from ethyl acetate and hexane to yield 8.13 g (Yield 89.1%) of the aimed compound (XXVI). mp. 139–140° C.

IR(KBr, ν max $cm^{-1}$) 3302, 1731, 1698, 1584, 1489, 1439, 1369, 1342, 1299, 1253, 1161, 1136, 1094, 835.

NMR ($CDCl_3$, δ ppm): 0.85(d, J=6.9 Hz, 3H), 1.00(d, J=6.9 Hz, 3H), 1.28(s, 9H), 2.05(m, 1H), 3.62(dd, J=4.2, 9.6 Hz, 1H), 5.08(d, J=9.6 Hz, 1H),6.97–7.05(m, 2H), 7.18–7.28(m, 4H), 7.40(m, 1H), 7.75–7.81(m, 2H).

$[\alpha]_D$–44.4±0.8 (c=1.008 $CHCl_3$ 24° C.)

Process 2

To a solution of the compound (XXVI, 3.23 g, 9.41 mmol) in dichloromethane (36 ml) was added trifluoroacetic acid (36 ml, 50×9.41 mmol) and the resulting mixture was stirred for 3 h at room temperature. After stirring for 5 h at room temperature, the solvent was removed under reduced pressure. The residue was crystallized from ethyl ether and hexane to obtain 2.62 g (yield 96.9%) of the aimed compound (XXVII) (mp. 137–138° C.)

IR(KBr, ν max $cm^{-1}$) 3154, 1728, 1688, 1583, 1488, 1251

NMR($CDCl_3$, δ ppm): 0.89(d, J=7.0 Hz, 3H), 0.98(d, J=6.8 Hz, 3H), 2.12(m, 1H), 3.80(dd, J=4.6, 9.6 Hz, 1H), 5.17(d, J=9.6 Hz, 1H), 6.95–7.08(m, 4H), 7.13–7.45(m. 3H), 7.70–7.85(m, 2H)

$[\alpha]_D$–3.7±0.4 (c=1.006 DMSO 24° C.)

Process 3

To a solution of the compound (XXVII, 0.3 g, 0.854 mmol) in dichloromethane (10 ml) were added oxaryl chloride (0.37 ml, 5×0.854 mmol) and a drop of dimethylformamide under ice-cooling and the resulting mixture was stirred for 1 h at room temperature. The reaction mixture was concentrated in vacuo and the residue was dissolved in 10 ml of tetrahydrofuran. A mixed solution of tetrahydrofuran (10 ml) and water (6 ml) including hydroxylamine hydrochloric acid (474 mg, 8×0.854 mmol) and sodium hydrogencarbonate (861 mg, 12×0.854 mmol) was stirred for 5 min under ice-cooling. To the mixed solution was added the above mentioned acid chloride solution under ice-cooling and the resulting mixture was stirred for 1 h at room temperature. The reaction mixture was extracted with ethyl acetate. The organic layer was washed with saturated sodium hydrogencarbonate aq., dried over sodium sulphate, and concentrated in vacuo. The residue was subjected to silica gel column chromatography and the fractions eluting with $CHCl_3/MeOH=20/1$ were collected, crystallized from hexane to yield 288 mg (Yield 92.5%) of the compound (1). The results are shown in Table 3.

EXAMPLE 2 to 6

The compounds (2) to (6) were synthesized in a manner similar to the above method. The results are shown in Table 3.

TABLE 3

| Referential example No. | Compound No. | [α]D (DMSO) | mp (° C.) | IR (ν cm⁻¹) (KBr) | Configuration of the asymmetric carbon |
|---|---|---|---|---|---|
| 1 | 1 | −11.2 ± 0.7 (25° C., c = 0.705) | 149–151 | 3628, 1634, 1584, 1488, 1336, 1253, 1157 | R |
| 2 | 2 | | 110–111 | 3323, 1678, 1328, 1150 | R |
| 3 | 3 | | 82–87 | 8410, 3276, 1724, 1582, 1488, 1331, 1152 (Nujol) | R |
| 4 | 4 | | 115–118 | 3302, 1667, 1324, 1153 (Nujol) | R |
| 5 | 5 | | 241–243 | 1734, 1719, 1324, 1160 | R |
| 6 | 6 | | 224–226 | 1750, 1324, 1159 | R |
| 7 | 7 | | 174–176 | 1735, 1503, 1343, 1163 | R |

EXAMPLE 7

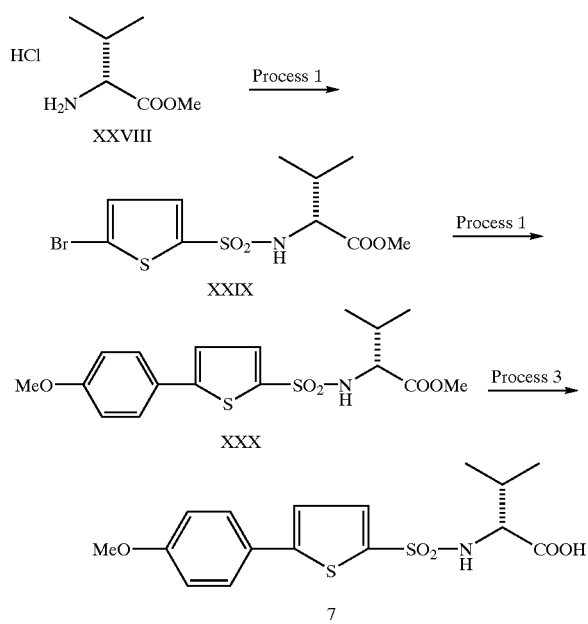

Process 1

To a solution of the compound (XXVIII, 755 mg, 4.5 mmol) in 12 ml of dichloromethane were added N-methylmorpholine (1.49 ml, 3×4.5 mmol) and 5-bromothiophen-2-sulfonylchloride (1.24 g, 1.05×4.5 mmol) under ice-cooling. After the reaction mixture was stirred for 15 h at room temperature, the resulting mixture was washed with 2N-hydrochloric acid, 5% sodium bicarbonate, and water. The organic layer was dried over sodium sulfate and concentrated in vacuo. The residue was subjected to the silica gel column chromatography and the fractions eluting with ethyl acetate/hexane=1/3 were collected, washed with n-hexane to obtain the aimed compound (XXIX, 1.32 g, yield 82%, mp. 109–110° C.).

[α]$_D$−34.5±0.7 (c=1.012 CHCl$_3$ 25° C.)

IR(CHCl$_3$, ν max cm⁻¹) 1737, 1356, 1164, 1138.

NMR(CDCl$_3$, δ ppm): 0.89(d, J=6.8 Hz, 3H), 1.00(d, J=6.8 Hz, 3H), 2.00 (m, 1H), 3.60(s, 3H), 3.83(dd, J=5.2, 10.0 Hz, 1H), 5.20(d, J=10.0 Hz, 1H), 7.04(d, J=4.1 Hz, 1H), 7.32(d, J=4.1 Hz, 1H).

Process 2

To a solution of the compound (XXIX, 500 mg, 1.4 mmol) in dry tetrahydrofuran (12 ml) were added powder potassium carbonate (387 mg, 2×1.4 mmol), 4-methoxyphenylboronic acid (319 mg, 1.5×1.4 mmol), and tetrakis(triphenylphosphine)palladium (81 mg, 0.05×1.4 mmol) and the resulting mixture was stirred for 48 h at 75° C. under argon. The reaction mixture was diluted with ethyl acetate. The organic layer was washed with 1N-hydrochloric acid, 5% sodium bicarbonate aq., and water, dried over sodium sulfate, and concentrated in vacuo. The residue was subjected to silica gel column chromatography and the fractions eluting with n-hexane/ethyl acetate=3/1 were collected, crystallized from n-hexane to obtain the aimed compound (XXX, 447 mg, yield 83%, mp. 122–123° C.).

Elemental analysis C$_{17}$H$_{21}$NO$_5$S$_2$ Calcd.: C; 53.25 H; 5.52 N; 3.65 S; 16.72 Found: C; 53.26 H; 5.50 N; 3.69 S; 16.63

[α]$_D$−21.7±0.6(c=1.000 DMSO 25° C.)

IR(KBr, ν max cm⁻¹) 1735, 1605, 1505, 1350, 1167, 1136.

NMR(CDCl$_3$, δ ppm): 0.90(d, J=7.0 Hz, 3H), 1.00(d, J=6.6 Hz, 3H), 2.10(m, 1H), 3.54(s, 3H), 3.85(s, 3H), 3.87(dd, J=5.0, 10.2 Hz, 1H), 5.20(d, J=10.2 Hz, 1H), 6.94(d, J=9.0 Hz, 2H), 7.52(d, J=9.0 Hz, 2H), 7.11(d, J=4.0 Hz, 1H), 7.49(d, J=4.0 Hz, 1H)

Process 3

To a solution of the compound (XXX, 390 mg, 1.01 mmol) in 8 ml of tetrahydrofuran and 8 ml of methanol was added 5.1 ml of 1N NaOH, and the resulting mixture was stirred at 60° C. for 6 h. The reaction mixture was concentrated in vacuo to remove the organic solvents. The resulting residue was diluted with ethyl acetate. The mixture was acidified with aqueous solution of citric acid and extracted with ethyl acetate. The organic layer was washed with brine, dried over sodium sulfate, and concentrated in vacuo to give 373 mg (yield 100%) of compound (7). The physical data were shown in Table 4.

EXAMPLE 8 to 30

The compounds (8) to (30) were synthesized in a manner similar to that described in the above method. The results are shown in Table 4.

TABLE 4

| Referential example No. | Compound No. | [α]D (DMSO) | mp (° C.) | IR (ν cm⁻¹) (KBr) | Configuration of the asymmetric carbon |
|---|---|---|---|---|---|
| 8 | 8 | +23.6 ± 0.6 (24° C., c = 1.000) | 226–230 | 3415, 1735, 1341, 1159 | R |
| 9 | 9 | | 182–187 | 3260, 1670, 1635, 1430, 1335, 1158 | R |
| 10 | 10 | −40.5 ± 1.6 (22° C., c = 0.504, MeOH) | 157.5–158.5 | 3431(br), 3280, 1690, 1606, 1352, 1168 | R |
| 11 | 11 | −38.5 ± 1.6 (22° C., c = 0.502, MeOH) | 140–141.5 | 3423(br), 3330, 1728, 1686, 1349, 1167 | R |
| 12 | 12 | −42.2 ± 1.6 (23° C., c = 0.505) | 198–202 | 3422, 3301, 1749, 1362, 1152 | R |
| 13 | 13 | −65.2 ± 2.1 (23° C., c = 0.505) | 194–198 | 3433, 3325, 1748, 1366, 1157 | R |
| 14 | 14 | +22.6 ± 1.2 (27° C., c = 0.504) | | 3390, 3303, 1746, 1609, 1322, 1156 | R |
| 15 | 15 | −24.1 ± 1.3 (24° C., c = 0.507) | 156–158 | 3433, 3330, 1736, 1699, 1346, 1162 | R |
| 16 | 16 | −18.2 ± 1.2 (27° C., c = 0.506) | 182–184 | 3297, 1701, 1606, 1346, 1162 | R |
| 17 | 17 | | 168–170 | 3277, 1719, 1606, 1346, 1159 | R |
| 18 | 18 | −1.2 ± 0.9 (26° C., c = 0.504) | 128–131 | 3433, 3277, 1715, 1606, 1341, 1158 | R |
| 19 | 19 | −2.0 ± 0.9 (26° C., c = 0.505) | 222–224 | 3310, 1752, 1609, 1319, 1159 | R |
| 20 | 20 | | 216–219 | 3269, 1710, 1608, 1323, 1150 | R |
| 21 | 21 | | 180–186 | 3345, 3306, 1710, 1607, 1354, 1154 | R |
| 22 | 22 | −2.0 ± 0.9 (26° C., c = 0.505) | 219–221 | 3310, 1752, 1609, 1319, 1159 | R |
| 23 | 23 | | 270–272 | 3280, 1723, 1607, 1436, 1335, 1157 | R |
| 24 | 24 | +3.0 ± 0.9 (27° C., c = 0.501) | 148–151 | 3493, 3240, 1714, 1329, 1162 | R |
| 25 | 25 | −18.4 ± 1.2 (27° C., c = 0.501) | 220–223 | 3288, 1716, 1607, 1432, 1320, 1157 | R |
| 26 | 26 | −13.4 ± 1.1 (27° C., c = 0.507) | 207–212 | 3431, 3279, 1709, 1607, 1343, 1163 | R |
| 27 | 27 | −22.2 ± 1.2 (27° C., c = 0.500) | 199–200 | 3463, 3270, 1736, 1608, 1319, 1156 | R |
| 28 | 28 | | 210–212 | 3333, 3276, 1747, 1610, 1316, 1151 | R |
| 29 | 29 | | 214–217 | 3426, 3357, 1714, 1608, 1330, 1152 | R |
| 30 | 30 | +15.6 ± 1.1 (26° C., c = 0.508) | >230 decomp. | 3417, 3296, 1744, 1322, 1155 | R |

EXAMPLE 4

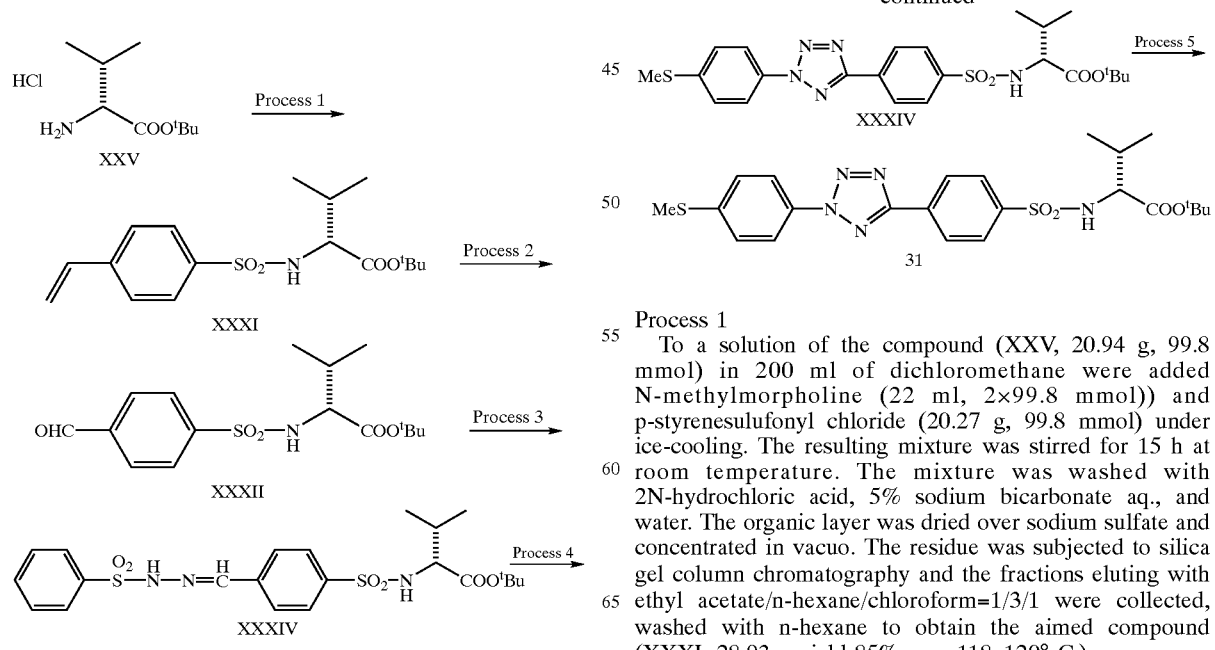

Process 1

To a solution of the compound (XXV, 20.94 g, 99.8 mmol) in 200 ml of dichloromethane were added N-methylmorpholine (22 ml, 2×99.8 mmol)) and p-styrenesulufonyl chloride (20.27 g, 99.8 mmol) under ice-cooling. The resulting mixture was stirred for 15 h at room temperature. The mixture was washed with 2N-hydrochloric acid, 5% sodium bicarbonate aq., and water. The organic layer was dried over sodium sulfate and concentrated in vacuo. The residue was subjected to silica gel column chromatography and the fractions eluting with ethyl acetate/n-hexane/chloroform=1/3/1 were collected, washed with n-hexane to obtain the aimed compound (XXXI, 28.93 g yield 85%, mp. 118–120° C.).

IR(KBr, ν max cm$^{-1}$) 3419, 3283, 1716, 1348, 1168.

NMR(CDCl$_3$, δ ppm): 0.85(d, J=6.9 Hz, 3H), 1.00(d, J=6.6 Hz, 3H), 1.21(s, 9H), 2.04(m, 1H), 3.62(dd, J=9.8, 4.5 Hz, 1H), 5.09(d, J=9.8 Hz, 1H), 5.41(dd, J=0.5, 10.9 Hz, 1H), 5.84(dd, J=0.5, 17.6 Hz, 1H), 6.72(dd, J=10.9, 17.6 Hz, 1H), 7.49(d, J=8.4 Hz, 2H), 7.79(d, J=8.4 Hz, 2H).

Process 2

A solution of the compound (XXXI, 5.09 g, 15 mmol) in dichloromethane (300 ml) was treated with ozone at −78° C. for 15 min. To the reaction mixture was added methylsulfide (22 ml, 20×15 mmol) and the resulting mixture was allowed to warm to room temperature gradually over 80 min and concentrated in vacuo to give 6.03 g of aldehyde derivative (XXXII).

IR(CHCl$_3$, ν max cm$^{-1}$) 3322, 1710, 1351, 1170.

NMR(CDCl$_3$, δ ppm): 0.85(d, J=6.9 Hz, 3H), 1.00(d, J=6.9 Hz, 3H), 1.22(s, 9H), 2.07(m, 1H), 3.69(dd, J=4.5, 9.9 Hz, 1H), 8.01(s, 4H), 10.08(s, 1H).

Process 3

To a solution of the compound (XXII, 6.02 g, 15 mmol) in 60 ml of ethanol and 15 ml of tetrahydrofuran was added 2.72 g (1.05×15 mmol) of benzenesulfonyl hydrazide at room temperature and the resulting mixture was stirred for 2 h. The reaction mixture was concentrated in vacuo. The residue was column chromatographed on silica gel and the fractions eluting with chloroform/ethyl acetate=1/4 were collected and recrystallized from ethyl acetate to give the aimed compound (XXXIII, 4.44 g, mp. 163–164° C., 60% yield from process 2).

Elemental analysis C$_{22}$H$_{29}$N$_3$O$_6$S$_2$ Calcd.: C; 53.32 H: 5.90 N: 8.48 S: 12.94 Found: C; 53.15 H; 5.87 N; 8.32 S; 12.82

[α]$_D$−11.6±1.0 (c=0.509 DMSO 23.5° C.)

IR(KBr, ν max cm$^{-1}$) 3430, 3274, 1711, 1364, 1343, 1172.

NMR(CDCl$_3$, δ ppm): 0.84(d, J=6.9 Hz, 3H), 0.99(d, J=6.6 Hz, 3H), 1.19(s, 9H), 2.00(m, 1H), 3.63(dd, J=4.5, 9.9 Hz, 1H), 5.16(d, J=9.9 Hz, 1H), 7.50–7.68(m, 5H), 7.73(s, 1H), 7.78–7.84(m, 2H), 7.96–8.02(m, 2H), 8.16(brs, 1H).

Process 4

To a solution of 4-(methylmercapto)aniline (0.14 ml, 1.11×1 mmol) in aqueous 50% ethanol was added 0.3 ml of conc. hydrochloric acid and the resulting mixture was stirred at 0 to 5° C. of the internal temperature. To the mixture was added a solution of sodium nitrite (78.4 mg, 1.14×1 mmol) in 1 ml of water and the resulting mixture was stirred for 15 min at the same temperature. To a solution of the compound (XXXIII, 496 mg, 1 mmol) in 5 ml of dry pyridine was added the above reaction mixture over 8 min at −25° C. This mixture was stirred for additional 4 h at −15° C. to room temperature, poured into water, and extracted with ethyl acetate. The organic layer was washed with 2N hydrochloric acid, 5% sodium bicarbonate aq., and water, dried over sodium sulfate, and concentrated in vacuo. The residue was column chromatographed on silica gel and the fractions eluting with chloroform/ethyl acetate=1/9 were collected to give the aimed compound (XXXIV, 374 mg, yield 74%).

Elemental analysis C$_{23}$H$_{29}$N$_5$O$_4$S$_2$·0.3H$_2$O Calcd.: C; 54.27 H; 5.86 N; 13.76 S; 12.60 Found: C; 54.25 H; 5.77 N; 13.87 S; 12.52

IR(KBr, ν max cm$^{-1}$) 3422, 3310, 1705, 1345, 1171.

NMR(d$_6$-DMSO, δ ppm): 0.83(d, J=6.9 Hz, 3H), 0.86(d, J=7.2 Hz, 3H), 1.19(s, 9H), 2.00(m, 1H), 2.59(s, 3H), 3.54(dd, J=6.3, 9.6 Hz, 1H), 7.56(d, J=8.7 Hz, 2H), 8.00(d, J=8.6 Hz, 2H), 8.10(d, J=8.7 Hz, 2H), 8.33(d, J=9.6 Hz, 2H), 8.34(d, J=8.7 Hz, 2H).

Process 5

A solution of the compound (XXXIV, 353 mg) in 2.5 ml of dichloromethane and 2.5 ml of trifluoroacetic acid was stirred for 3 h at room temperature. The reaction mixture was concentrated in vacuo and the resulting residue was washed with ethyl ether to give the compound (31, 308 mg, yield 98%). The results are shown in Table 5.

EXAMPLES 32 to 62

The compounds (32) to (62) were synthesized in a manner similar to that described in the above method. The results are shown in Tables 5 and 6.

TABLE 5

| Referential example No. | Compound No. | [α]D (DMSO) | mp (° C.) | IR (ν cm$^{-1}$) (KBr) | Configuration of the asymmetric carbon |
|---|---|---|---|---|---|
| 31 | 31 | | 194–195 | 1720, 1343, 1166 | R |
| 32 | 32 | | 215–216 | 3700–2200, 3278, 1634, 1337, 1160 | R |
| 33 | 33 | −2.8 ± 0.9 (21.5° C., c = 0.499) | 194–195 | 3700–2200, 3278, 1634, 1337, 1160 | R |
| 34 | 34 | | 188–190 | 2500–3600, 3445, 3325, 2104, 1727, 1687, 1347, 1168 | R |
| 35 | 35 | +17.9 ± 1.1 (22° C., c = 0.508) | 195–196 | 3700–2200(br), 3411, 3271, 1749, 1719, 1331, 1165 | R |
| 36 | 36 | +16.0 ± 0.6 (22° C., c = 1.004) | 203–205 | 3394, 1757, 1738, 1331, 1163 | R |
| 37 | 37 | +18.7 ± 0.6 (25° C., c = 1.005) | 199–201 | 3468, 1718, 1685, 1334, 1170 | R |
| 38 | 38 | −9.9 ± 1.0 (24° C., c = 0.503) | 227–228 | 3422, 3289, 1696, 1348, 1171 | R |
| 39 | 39 | −10.7 ± 1.0 (24.5° C., c = 0.504) | 208–209 | 3700–2200(br), 3260, 1746, 1726, 1715, 1334, 1170 | R |
| 40 | 40 | −22.9 ± 1.2 (23° C., c = 0.510) | 205–207 | 3413, 1700, 1314, 1157 | R |
| 41 | 41 | −1.7 ± 0.4 (24° C., c = 1.001) | 205–207 | 3286, 1730, 1343, 1165 | R |
| 42 | 42 | | 197–200 | 3255, 1650, 1510, 1333, 1165 | R |
| 43 | 43 | −3.9 ± 0.4 | 208–210 | 3452, 3351, 1715, 1347, 1167 | R |

TABLE 5-continued

| Referential example No. | Compound No. | [α]D (DMSO) | mp (° C.) | IR (ν cm⁻¹) (KBr) | Configuration of the asymmetric carbon |
|---|---|---|---|---|---|
| 44 | 44 | (24° C., c = 1.000) | 189–191 | 3441, 3296, 1726, 1686, 1346, 1168 | R |
| 45 | 45 | −33.4 ± 1.5 (22° C., c = 0.5009 MeOH) | 188.5–189.5 | 3432m3292, 1714, 1688, 1347, 1165 | R |
| 46 | 46 | −31.3 ± 1.4 (22° C., c = 0.508 MeOH) | 175–177 | 3372, 3334, 3281, 1730, 1712, 1348, 1173 | R |
| 47 | 47 | −9.5 ± 0.5 (24° C., c = 1.003) | 220–222 | 3446, 3350, 1711, 1347, 1170 | R |
| 48 | 48 | −16.1 ± 1.1 (24° C., c = 1.000) | 217–219 | 3358, 3249, 1726, 1336, 1163 | R |
| 49 | 49 | +1.8 ± 0.8 (24° C., c = 0.504) | 217–220 | 3333, 1697, 1732, 1344, 1170 | S |
| 50 | 50 |  | 217–219 | 3437, 3332, 1732, 1695, 1345, 1169 | S |
| 51 | 51 | −9.3 ± 1.0 (25° C., c = 0.504) | 204–206 | 3289, 1696, 1348, 1175 | R |

TABLE 6

| Referential example No. | Compound No. | [α]D (DMSO) | mp (° C.) | IR (ν cm⁻¹) (KBr) | Configuration of the asymmetric carbon |
|---|---|---|---|---|---|
| 52 | 52 | −32.9 ± 1.5 (25° C., c = 0.504) | 152–154 | 3298, 1739, 1337, 1163 | R |
| 53 | 53 | −11.3 ± 1.0 (26° C., c = 0.503) |  | 3289, 2231, 1749, 1345, 1167 | R |
| 54 | 54 | −9.5 ± 1.0 (25° C., c = 0.508) | 192–193 | 3329, 1728, 1370, 1172 | R |
| 55 | 55 | −11,5 ± 1.0 (25° C., c = 0.500) |  | 3437, 1686, 1609, 1340, 1169 | R |
| 56 | 56 | −8.8 ± 1.0 (25° C., c = 0.500) |  | 3262, 1716, 1653, 1337, 1170 | R |
| 57 | 57 | +2.4 ± 0.9 (25° C., c = 0.501) | 198–200 | 3268, 1709, 1346, 1165 | R |
| 58 | 58 | −21.7 ± 1.1 (26° C., c = 0.503) |  | 3342, 1719, 1683, 1315, 1161 | R |
| 59 | 59 |  | 163–165 | 3214, 1756, 1724, 1345, 1164 | R |
| 60 | 60 | −105.4 ± 2.9 (27° C., c = 0.501) | 216–219 | 3334, 3165, 1740, 1341, 1162 | R |
| 61 | 61 | −3.8 ± 0.9 (27° C., c = 0.506) | 184–187 | 3190, 1744, 1512, 1313, 1148 | R |
| 62 | 62 | −5.0 ± 0.9 (27° C., c = 0.503) | 204–207 | 3285, 1717, 1652, 1604, 1425, 1342, 1169 | R |

EXAMPLE 63

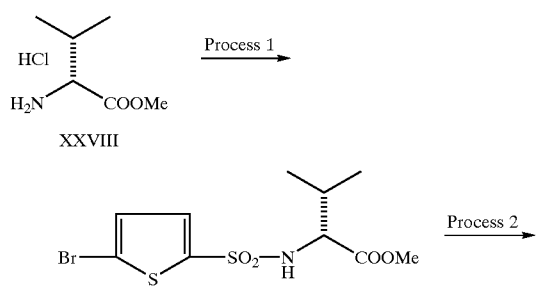

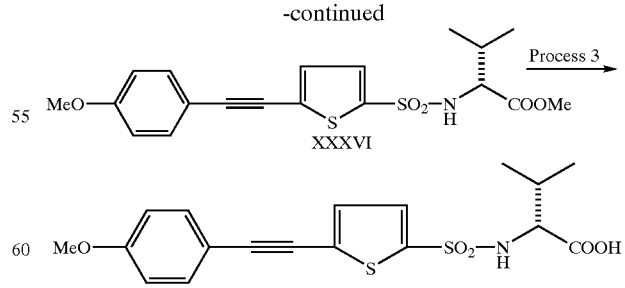

Process 1

To a solution of the compound (XXV, 755 mg, 4.5 mmol) in 12 ml of dichloromethane were added N-methylmorpholine (1.49 ml, 3×4.5 mmol) and 5-bromothiophen-2-sulfonyl chloride (1.24 g, 1.05×4.5 mmol) under ice-cooling. After stirring for 15 h at room temperature, the mixture was washed with 2N-hydrochloric acid, 5% sodium bicarbonate aq., and water. The organic layer was dried over sodium sulfate and concentrated in vacuo. The resulting residue was subjected to silica gel column chromatography and the fractions eluting with ethyl acetate/n-hexane=1/3 were collected, washed with n-hexane to obtain the aimed compound (XXXV, 1.32 g yield 82%, mp. 109–110° C.).

$[\alpha]_D$ –34.5±0.7(c=1.012 $CHCl_3$ 25° C.)

IR($CHCl_3$, ν max $cm^{-1}$) 1737, 1356, 1164, 1138.

NMR($CDCl_3$,δ ppm): 0.89(d, J=6.8 Hz, 3H), 1.00(d, J=6.8 Hz, 3H), 2.00 (m, 1H), 3.60(s, 3H), 3.83(dd, J=5.2, 10.0 Hz, 1H), 5.20(d, J=10.0 Hz, 1H), 7.04(d, J=4.1 Hz, 1) 7.32(d, J=4.1 Hz, 1H).

Process 2

To a degassed solution of the compound (XXXV, 400 mg, 1.12 mmol) in 5 ml of dimethylformamide were added 4-methoxyphenylacetylene (222 mg, 1.5×1.12 mmol) and copper iodide (I) (21 mg, 0.1×1.12 mmol) under an argon atmosphere. Bis(triphenylphosphine)palladium dichloride (II) (39 mg, 0.05×1.12 mmol) and triethylamine (0.47 ml, 3×1.12 mmol) were added to the reaction mixture. The resulting mixture was degassed and stirred overnight under an argon atmosphere at 50° C. The reaction mixture was diluted with ethyl acetate. The organic later was washed with 1N-hydrochloric acid, 5% sodium bicarbonate, and water, dried over sodium sulfate, and concentrated in vacuo. The resulting residue was column chromatographed on silica gel.

The fractions eluting with n-hexane/ethyl acetate=2/1 were collected and recrystallized from ethyl acetate/n-hexane to give the aimed compound (XXXVI, 392 mg, yield 86%, mp. 131–132° C.).

Elemental analysis $C_{19}H_{21}NO_5S_2$.0.2 $H_2O$ Calcd.: C; 55.51 H; 5.25 N; 3.41 S; 15.60 Found: C; 55.80 H; 5.19 N; 3.38 S; 15.36

IR(KBr, ν max $cm^{-1}$) 3268, 2203, 1736, 1604, 1524, 1348, 1164.

NMR($CDCl_3$,δ ppm): 0.90(d, J=6.6 Hz, 3H), 1.00(d, J=7.0 Hz, 3H), 2.00(m, 1H), 3.60(s, 3H), 3.84(s, 3H), 3.86(dd, J=5.0, 10.2 Hz, 1H), 5.21(d, J=10.2 Hz, 1H), 6.90(d, J=9.0 Hz, 2H), 7.44(d, J=9.0 Hz, 2H), 7.12(d, J=4.0 Hz, 1H), 7.44(d, J=4.0 Hz, 1H).

Process 3

To a solution of the compound (XXXVI, 407 mg, 1 mmol) in 8 ml of tetrahydrofuran and 8 ml of methanol was added 5.1 ml of 1N NaOH. The resulting mixture was stirred for 6 h at 60° C. The reaction mixture was concentrated in vacuo to remove an organic solvent, and the residue was diluted with ethyl acetate. The mixture was acidified with aqueous solution of citric acid and extracted with ethyl acetate. The organic layer was washed with brine, dried over sodium sulfate, and concentrated in vacuo to give compound (63, 373 mg, yield 100%). The results are shown in Table 7.

EXAMPLES 64 to 89

The compounds (64) to (89) were synthesized in a manner similar to that described in the above method. The results are shown in Tables 7 and 8.

TABLE 7

| Referential example No. | Compound No. | [α]D (DMSO) | mp (° C.) | IR (ν $cm^{-1}$) (KBr) | Configuration of the asymmetric carbon |
|---|---|---|---|---|---|
| 63 | 63 | | 194–195 | 1710, 1604, 1351, 1216 | R |
| 64 | 64 | −7.6 ± 100 (25° C., c = 0.503) | 157–158 | 3268, 2208, 1712, 1430, 1414, 1350, 1163, 1143 | R |
| 65 | 65 | | 191–193 | 3290, 3200, 1670, 1650 (Nujol) | R |
| 66 | 66 | −3.5 ± 0.4 (22° C., c = 1.004) | 153–154 | 3280, 3234, 1723, 1486, 1423, 1345, 1228, 1150, 1115, 1088, 1014, 830, 811, 699 | R |
| 67 | 67 | | 149–150 | 1695, 1334, 1184 | R |
| 68 | 68 | | 180–182 | 1729, 1675, 1340, 1168 | R |
| 69 | 69 | | | 1605, 1523, 1340, 1151 | R |
| 70 | 70 | | 201–202 | 3389, 3370, 2207, 1666, 1427, 1329, 1161 | R |
| 71 | 71 | | 182–187 | 3260, 1670, 1635, 1335, 1160 | R |
| 72 | 72 | | | 3410, 2919, 2207, 1668, 1593, 1519, 1487, 1457, 1426 | R |
| 73 | 73 | +19.8 ± 0.6 (23° C., c = 1.008) | 227–229 | 1736, 1618, 1398, 1168 | R |
| 74 | 74 | | 196–199 | 3408, 3381, 3296, 3264, 2218, 1676, 1642, 1605, 1590, 1568, 1556, 1516, 1457, 1425 | R |
| 75 | 75 | −8.4 ± 0.5 (22.5° C., c = 1.005) | 148–149 | 3329, 2209, 1703, 1351, 1167 | R |
| 76 | 76 | +21 ± 0.6 (22.5° C., c = 1.012) | 171–173 | 3431, 2205, 1713, 1353, 1161 | R |
| 77 | 77 | −6.6 ± 0.5 (23° C., c = 1.008) | 208–209 | 3335, 2202, 1733, 1351, 1163 | R |
| 78 | 78 | +20.1 ± 0.6 (23° C., c = 1.000) | | 3383, 2202, 1747, 1323, 1158 | R |
| 79 | 79 | −15.6 ± 0.6 (23° C., c = 1.001) | 156–157 | 3260, 2206, 1709, 1351, 1162 | R |
| 80 | 80 | | | 3410, 2207, 1668, 1593, 1338, 1156 | |

TABLE 7-continued

| Referential example No. | Compound No. | [α]D (DMSO) | mp (° C.) | IR (ν cm⁻¹) (KBr) | Configuration of the asymmetric carbon |
|---|---|---|---|---|---|
| 81 | 81 | +10.3 ± 1.0 (26° C., c = 0.504) | 218–219 | 3459, 3384, 2208, 1720, 1338, 1159 | R |
| 82 | 82 | | | 3412, 3257, 2202, 1741, 1604, 1338, 1156 | R |
| 83 | 83 | +19.9 ± 0.6 (24° C., c = 1.007) | 224–226 | 3406, 3254, 2203, 1723, 1341, 1161 | R |

TABLE 8

| Referential example No. | Compound No. | [α]D (DMSO) | mp (° C.) | IR (ν cm⁻¹) (KBr) | Configuration of the asymmetric carbon |
|---|---|---|---|---|---|
| 84 | 84 | −8.9 ± 0.5 (24° C., c = 1.000) | 204–207 | 3518, 3227, 2205, 1712, 1330, 1162 | R |
| 85 | 85 | −4.6 ± 0.5 (24° C., c = 1.002) | 215–217 | 3491 3263, 2207, 1720, 1354, 1338, 1160 | R |
| 86 | 86 | +18.5 ± 2.9 (26° C., c = 0.205) | 214–218 | 3402, 3308, 2199, 1736, 1380, 1344, 1162 | R |
| 87 | 87 | −12.4 ± 1.0 (27° C., c = 0.502) | 158–160 | 3336, 3166(br), 2193, 1735, 1698, 1377, 1164 | R |
| 88 | 88 | +22.7 ± 1.3 (25° C., c = 0.500) | 227–229 | 3600–2400(br), 1736, 1618, 1398, 1168 | R |
| 89 | 89 | | 196–199 | 3296, 2218, 1676, 1642, 1376, 1355, 1164 | R |

EXAMPLE 90

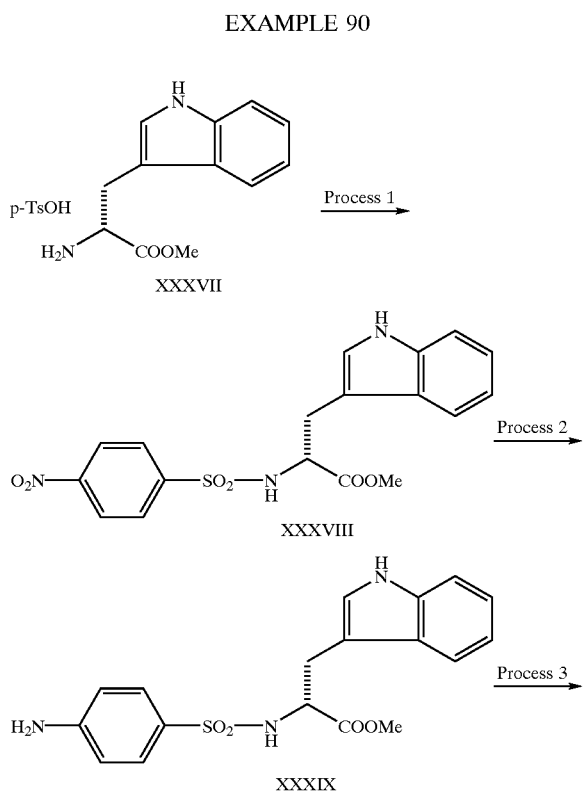

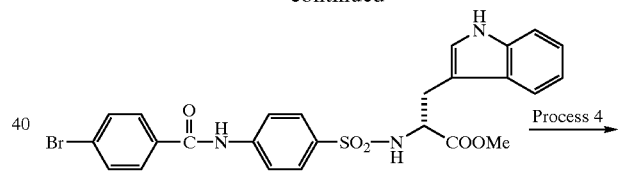

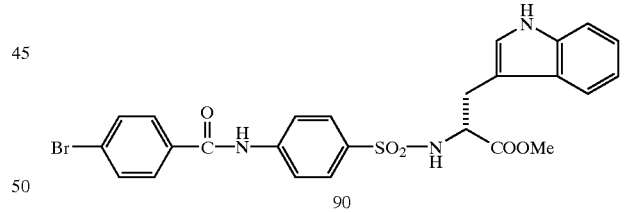

Process 1

To a solution of the compound (XXXVII, 5.0 g, 12.8 mmol) in 50 ml of dichloromethane were added N-methylmorpholine (4.2 ml, 3×12.8 mmol), p-nitrobenzenesulfonyl chloride (3.78 g, 1.2×12.8 mmol) under ice-cooling. The reaction mixture was stirred over night and washed with 2N-hydrochloric acid, 5% sodium bicarbonate aq., and water. The organic layer was dried over sodium sulfate and concentrated in vacuo. The resulting residue was recrystallized from acetone—n-hexane to obtain the aimed compound (XXXVIII, 5.05 g, yield 97.8%, mp. 172–174° C.)

IR(KBr, ν max cm⁻¹) 3417, 3281, 1745, 1529, 1353, 1168.

NMR(d₆-DMSO, δ ppm): 2.85(dd, J=9.8, 14.6 Hz, 1H), 3.08(dd, J=4.8, 14.4 Hz, 1H), 3.56(s, 3H), 4.02(m, 1H), 6.84–7.30(m, 5H), 7.53(d, J=8.6 Hz, 2H), 7.94(d, J=8.6 Hz, 2H), 8.83(brs, 1H), 10.37(s, 1H).

[α]$_D$+43.5±1.6(c=0.508 DMSO 25° C.)

Process 2

A solution of the compound (XXXVIII, 5.0 g) in 50 ml of methanol and 10 ml of dimethylformamide was hydrogenated using 10% Pd/C (1 g) for 1 h at room temperature. The reaction mixture was filtered off and the filtrate was concentrated in vacuo. The residue was recrystallized from chloroform/ethyl ether to give the aimed compound (XXXIX, 3.43 g, yield 74.1%, mp. 158–160° C.)

IR(KBr, ν max cm$^{-1}$) 3468, 3378, 3283, 1737, 1623, 1596, 1335, 1320, 1155.

NMR(d$_6$-DMSO, δ ppm): 2.85(dd, J=6.6, 14.2 Hz, 1H), 3.00(dd, J=8.2, 14.2 Hz, 1H), 3.30(s, 3H), 3.86(m, 1H), 5.93(s, 2H), 6.56(d, J=8.8, 2H), 6.90–7.10(m, 3H), 7.20–7.38(m, 2H).

[α]$_D$+10.1±1.0(c=0.503 DMSO 25° C.)

Process 3

To a solution of the compound (XXXIX, 500 mg, 1.3 mmol) in 13 ml of dichloromethane were added N-methylmorpholine (0.29 ml, 2×1.3 mmol) and p-bromobenzoyl chloride (371 mg, 1.3×1.3 mmol) under ice-cooling and the resulting mixture was stirred over night at room temperature. Methyl ethyl ketone was added to the reaction mixture and the mixture was washed with 2N-hydrochloric acid, 5% sodium bicarbonate aq., and water. The organic layer was dried over sodium sulfate and concentrated in vacuo. The residue was recrystallized from acetone—n-hexane to give the aimed compound (XL, 720 mg, yield 100%, mp. 215–218° C.)

IR(KBr, ν max cm$^{-1}$) 3397, 3330, 1787, 1732, 1668, 1348, 1337, 1157.

NMR(d$_6$-DMSO, δ ppm): 2.90(dd, J=8.0, 13.4 Hz, 1H), 3.33(s, 3H), 3.06(dd, J=7.0, 14.8 Hz, 1H), 2.97(dt, J=8.2, 8.2 Hz, 1H), 6.90–7.10(m, 3H), 7.24–7.22(m, 2H), 7.62(d, J=8.8 Hz, 2H), 7.78(d, J=8.4 Hz, 2H), 7.86(d, J=8.4 Hz, 2H), 7.93(d, J=8.8 Hz, 2H), 8.07(d, J=8.8 Hz, 1H, 8.39(d, J=8.8 Hz, 1H), 10.59(s, 1H).

[α]$_D$−1.9±0.8(c=0.51 DMSO 25° C.)

Process 4

To a solution of the compound (XL, 807 mg) in 6 ml of dimethylsulfoxide was added 2.9 ml of 1N NaOH. The resulting mixture was stirred for 5 h at room temperature. Water was added to the mixture and acidified with 2N-hydrochloric acid. The precipitated crystal are collected and washed with water to give compound (90, 720 mg, yield 78.7%). The results are shown in Table 9.

EXAMPLE 91 to 94

The compounds (91) to (94) were synthesized in a manner similar to that described in the above method. The results are shown in Table 9.

TABLE 9

| Referential example No. | Compound No. | [α]D (DMSO) | mp (° C.) | IR (ν cm$^{-1}$) (KBr) | Configuration of the asymmetric carbon |
|---|---|---|---|---|---|
| 90 | 90 | +3 0 ± 0.9 (250G, c = 0.501) | 215–218 | 2800–3640, 3328, 1727, 1668, 1590, 1514, 1316, 1154 | R |
| 91 | 91 | | 211–213 | 1719, 1629, 1340, 1156 | R |
| 92 | 92 | | 170–175 | 1730, 1651, 1603, 1333, 1161 | R |
| 93 | 93 | | 242–244 | 2840–3600, 3346, 1752, 1726, 1656, 1610, 1324, 1160 | R |
| 94 | 94 | | 235–235.5 | 2550–3600, 3318, 1742, 1667, 1591, 1334, 1161 | R |

EXAMPLE 95 to 100

The compounds (95) to (100) were synthesized in a manner similar to that described in WO 97/27174 and the above method. The results are shown in Table 10.

TABLE 10

| Referential example No. | Compound No. | [α]D (DMSO) | mp (° C.) | IR (ν cm$^{-1}$) (KBr) | Configuration of the asymmetric carbon |
|---|---|---|---|---|---|
| 95 | 95 | −29.4 ± 1.4 (25° C., c = 0.504) | 166–169 | 3437, 1737, 1376, 1162 | R |
| 96 | 96 | −32.0 ± 1.4 (25° C., c = 0.503) | 178–179 | 3280, 1702, 1351, 1165 | R |
| 97 | 97 | −9.2 ± 1.0 (25° C., c = 0.503) | 184–186 | 3282, 1711, 1354, 1164 | R |
| 98 | 98 | | 220–223 | 3202, 1748, 1707, 1376, 1156 | R |
| 99 | 99 | −9.1 ± 1.0 (26° C., c = 0.504) | 227–230 | 3258, 1725, 1352, 1159 | R |

TABLE 10-continued

| Referential example No. | Compound No. | [α]D (DMSO) | mp (° C.) | IR (ν cm$^{-1}$) (KBr) | Configuration of the asymmetric carbon |
|---|---|---|---|---|---|
| 100 | 100 | −6.2 ± 0.9 (24° C., c = 0.503) | 203–205 | 3437, 3318, 1709, 1343, 1162 | R |

EXAMPLE 101

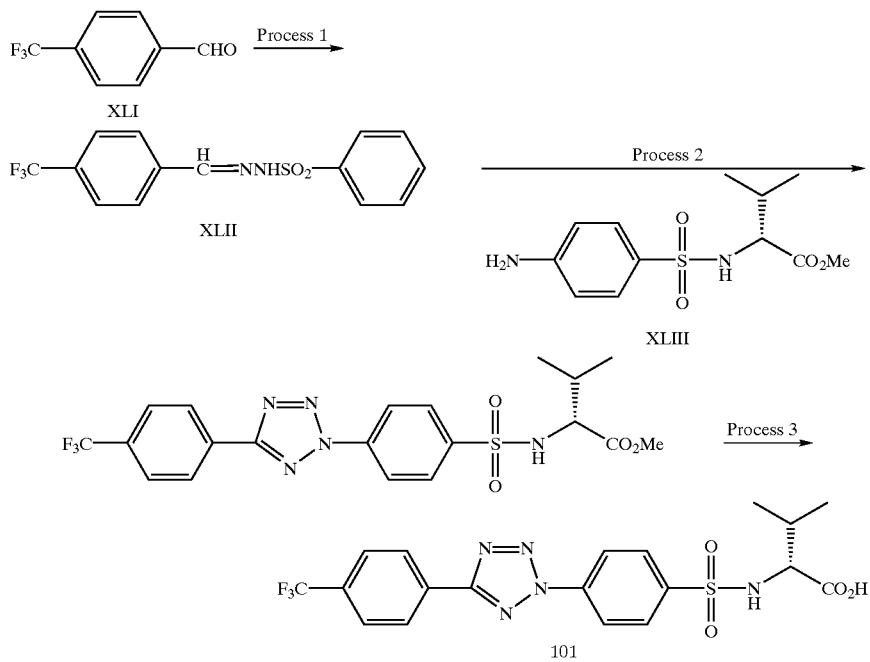

Process 1

A solution of benzenesufonylhydrazide (1.722 g, 10 mmol) and the compound (XLI, 1.43 ml, 1.05×10 mmol) in 20 ml of ethanol and 2 ml of tetrahydrofuran was stirred for 3 h at room temperature. Water was added to the reaction mixture and the mixture was extracted with ethyl acetate. The organic layer was washed with 2N-hydrochloric acid, brine, and brine, dried over sodium sulfate, and concentrated in vacuo. The residue was crystallized from hexane/ethyl acetate to give the compound (XLII, 2.873 g, yield 87.5%, 142–144° C.).

IR(KBr, ν max cm$^{-1}$) 3431, 3178, 1325, 1169, 1123.

$^1$H NMR (CDCl$_3$, δ ppm): 7.51–7.72 (m, 2H), 7.79 (s, 1H), 7.98–8.04 (m, 2H), 8.24 (br s, 1H).

Elemental analysis C$_{14}$H$_{11}$F$_3$N$_2$O$_2$S Calcd.: C;51.22, H;3.38, F;17.36, N;8.53, S;9.77 Found: C;51.22, H;3.38, F;17.50, N;8.59, S;9.69

Process 2

To a solution of the compound (XLIII, 572 mg, 2 mmol) in 20 ml of 50% ethanol aq. was added 0.84 ml of conc. hydrochloric acid and the resulting mixture was stirred at 0 to 5° C. of the internal temperature. To the mixture was added a solution of sodium nitrite (168 mg, 1.2×2 mmol) in 3 ml of water and the resulting mixture was stirred for 20 min at the same temperature. A solution of the compound (XLII, 657 mg, 2 mmol) in 20 ml of pyridine was stirred at −25° C. To the pyridine solution was added to the above reaction mixture and the resulting mixture was stirred for 1 h at the same temperature and stirred over night at room temperature. Water was added to the reaction mixture and the resulting mixture was extracted with ethyl acetate. The organic layer was washed with 2N hydrochloric acid, 1N potassium hydroxide, and saturated brine, dried over sodium sulfate, and concentrated in vacuo. The residue was column chromatographed on silica gel and the fractions eluting with chloroform/methanol=50/1 were collected, recrystallized from acetone/hexane to give compound (XLIV, 637 mg, yield 65.9%, mp. 189–191° C.).

IR(KBr, ν max cm$^{-1}$) 3282, 1735, 1350, 1328, 1165, 1127.

$^1$H NMR (CDCl$_3$, δ ppm): 0.90 (d, J=6.9 Hz, 3H), 1.00 (d, J=6.6 Hz, 3H), 2.10 (m, 1H), 3.52 (s, 3H), 3.85 (dd, J=4.8, 9.9 Hz, 1H), 5.23 (d, J=9.9 Hz, 1H), 7.79–7.85 (m, 2H), 8.05–8.10 (m, 2H), 8.36–8.42 (m, 4H).

[α]$_D$+3.9±0.9 (c=0.512, DMSO, 25° C.)

Elemental analysis C$_{20}$H$_{20}$F$_3$N$_5$O$_4$S Calcd.: C; 49.69, H; 4.17, F; 11.79, N; 14.49, S; 6.63 Found: C; 49.52, H; 4.17, F; 11.73, N; 14.50, S; 6.66

Process 3

To a solution of the compound (XLIV, 637 mg, 1.32 mmol) in 8 ml of tetrahydrofuran and 8 ml of methanol was added 1N KOH. The resulting mixture was stirred over night at 60° C. The reaction mixture was acidified with 2N hydrochloric acid and extracted with ethyl acetate. The organic layer was washed with brine, dried over sodium sulfate, and concentrated in vacuo. The residue was recrystallized from acetone/hexane to give compound (101, 585 mg, yield 94.4%, mp. 198–200° C.). The results are shown in Table 11.

EXAMPLE 102 to 121

The compounds (102) to (121) were synthesized in a manner similar to that described in the above method. The results are shown in Table 11.

administered once a day from the next day. The rats were housed in stainless metabolic cages just after the administration of test compound, and then 24-hour urine samples were collected. After measuring the volume, the urine was centrifuged at 3000 rpm for 10 min at room temperature. The supernatant was used for the determination of urinary excretion of protein. Urinary protein was determined by pyrogallole red method (Micro TP-test Wako, Wako Zyunyaku). The amount of urinary protein excretion on day 2 in compound-treated group was compared with that in vehicle-

TABLE 11

| Referential example No. | Compound No. | [α]D (DMSO) | mp (° C.) | IR (ν cm$^{-1}$) (KBr) | Configuration of the asymmetric carbon |
|---|---|---|---|---|---|
| 101 | 101 | −4.2 ± 0.9 (27° C., c = 0.506) | 203–208 | 3430, 3290, 1701, 1610, 1344, 1164 | R |
| 102 | 102 | −9.1 ± 1.0 (26° C., c = 0.504) | 224–226 | 3409, 3329, 1741, 1610, 1590, 1321, 1163 | R |
| 103 | 103 | −17.4 ± 1.1 (27° C., c = 0.506) | 248–245 | 3335, 1725, 1348, 1168 | R |
| 104 | 104 | −7.7 ± 1.0 (25° C., c = 0.504) | 198–200 | 3270, 1746, 1326, 1160 | R |
| 105 | 105 | | 190–192 | 3339, 3287, 1719, 1690, 1350, 1167 (Nujol) | R |
| 106 | 106 | −9.4 ± 1.0 (25° C., c = 0.500) | 204–205 | 3317, 3232, 1762, 1746, 1379, 1167 (Nujol) | R |
| 107 | 107 | −11.7 ± 1.0 (25° C., c = 0.505) | 186–187 | 3302, 3215, 1762, 1746, 1378, 1161 (Nujol) | R |
| 108 | 108 | −2.2 ± 0.8 (25° C., c = 0.505) | 187–189 | 3184, 1739, 1322, 1146 (Nujol) | R |
| 109 | 109 | +31.9 ± 1.4 (25° C., c = 0.502) | 125–126 | 3384, 3268, 1761, 1712, 1332, 1159 (Nujol) | R |
| 110 | 110 | | 188–190 | 3182, 1739, 1322, 1146 (Nujol) | S |
| 111 | 111 | +33.7 ± 1.5 (25° C., c = 0.504) | 113–115 | 3286, 1732, 1683, 1328, 1162 (Nujol) | R |
| 112 | 112 | +7.8 ± 1.0 (25° C., c = 0.502) | 179–181 | 3293, 1713, 1348, 1145 (Nujol) | S |
| 113 | 113 | −6.8 ± 0.9 (25° C., c = 0.504) | 153–154 | 3149, 1741, 1709, 1324, 1146 (Nujol) | R |
| 114 | 114 | | 194–195 | 3269, 1709, 1351, 1152 (Nujol) | R |
| 115 | 115 | | 191–192 | 3445, 3288, 1719, 1670, 1595, 1450, 1350, 1163 | R |
| 116 | 116 | | 199–201 | 3316, 2962, 1715, 1341, 1156 | R |
| 117 | 117 | | 155–157 | 3272, 1709, 1350, 1152 | R |
| 118 | 118 | −7.9 ± 1.0 (26° C., c = 0.504) | 187–189 | 3316, 1744, 1309, 1161 | R |
| 119 | 119 | −8.0 ± 1.0 (26° C., c = 0.503) | 185–188 | 3284, 1726, 1370, 1167, | R |
| 120 | 120 | −9.1 ± 1.0 (26° C., c = 0.504) | 194–196 | 3313, 1739, 1343, 1164 | R |
| 121 | 121 | −9.6 ± 1.0 (26° C., c = 0.502) | 191–193 | 3263, 1746, 1329, 1159 | R |

TEST EXAMPLE

TEST EXAMPLE 1

5-week-old male Slc-Wistar rats were reared under the conditions of room temperature of 25° C., 40–60% humidity and 12 hour cycles of light and darkness and fed on solid chow (CA-1, Clea Japan) and tap water ad libitum. After one week's preliminary rearing, each rat was housed in a stainless metabolic cage for acclimation for one week, and was used for experiment at 7 weeks of old (body weight: 150–180 g). E30 monoclonal antibody (J.J.N., vol. 36, p106, 1994) was diluted with saline at 100 μg/0.4 ml and was administered from tail vein at the volume of 0.4 ml/body. Compound (2) was suspended with 5% gum arabic solution and was given at the dose of 100 mg 2 hours before E30 injection. Subsequently, compound (2) of 100 mg was orally treated one, and inhibitory ratio of urinary protein excretion was calculated. The results are shown in Table 11. The compounds (1) and (3) to (121) were examined in a manner similar to that described in the above method and the results are shown in Table 12. FIG. 1 shows the change in urinary excretion of protein throughout the experiment.

TABLE 12

| Compound No. | Inhibitory rate (%) |
|---|---|
| 1 | 44.6 |
| 2 | 31.1 |
| 3 | 28.9 |
| 4 | 56.3 |

TABLE 12-continued

| Compound No. | Inhibitory rate (%) |
| --- | --- |
| 5 | 21.6 |
| 6 | 27.1 |
| 7 | 48.0 |
| 8 | 14.4 |
| 9 | 30.5 |
| 10 | 2 |
| 11 | 12.2 |
| 12 | 33.4 |
| 13 | 17.8 |
| 16 | 32 |
| 24 | 11.5 |
| 26 | 10.7 |
| 31 | 40.9 |
| 32 | 56.5 |
| 33 | 25.5 |
| 35 | 50.7 |
| 36 | 22.1 |
| 37 | 33.6 |
| 38 | 29.4 |
| 39 | 49.7 |
| 40 | 10.2 |
| 41 | 16 |
| 44 | 19 |
| 63 | 36.0 |
| 64 | 36.7 |
| 65 | 37.6 |
| 66 | 31.3 |
| 67 | 13.5 |
| 69 | 25.5 |
| 70 | 25.8 |
| 71 | 30.4 |
| 72 | 21.1 |
| 73 | 14 |
| 80 | 21.1 |
| 81 | 9 |
| 82 | 22.8 |
| 84 | 26.6 |
| 86 | 34 |
| 88 | 25.6 |
| 89 | 36.5 |
| 90 | 31.2 |
| 91 | 52.0 |
| 92 | 54.3 |
| 93 | 29.3 |
| 94 | 21.5 |
| 95 | 21 |
| 101 | 29 |
| 104 | 27 |
| 108 | 35 |
| 114 | 2.7 |

Figure 2:
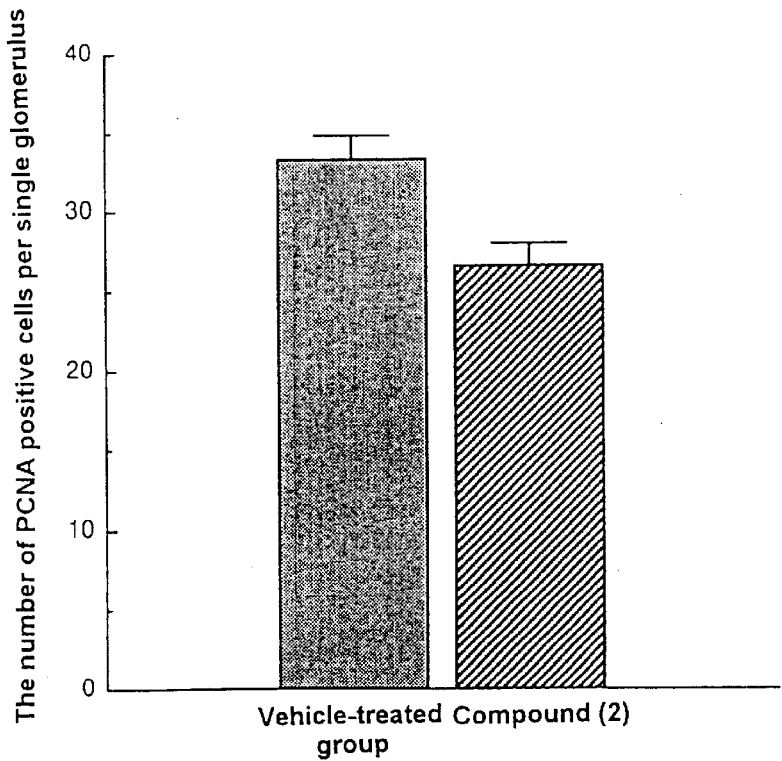
FIG. 2 shows the number of PCNA positive cells per single glomerulus in non-treated group and test compound-treated one 5 days after the initiation of experiment.

On the follow-up day (day 5), animals were subjected to ventrotomy under anesthesia with pentobarbital, and then, kidneys were removed immediate after blood collection, fixed in 10% formalin or methacarn solution. The tissue samples fixed with formalin were embedded in paraffin. Sections were stained with the periodic acid-Schiff reaction and processed for light microscopy. On the other hand, the paraffin sections of tissue samples fixed with methacarn solution were processed for immunohistochemistry with anti-PCNA antibody (mouse anti-PCNA IgG). After then, the number of PCNA positive glomerular cells belonging to S phase within the cell cycle were counted. The result is shown in FIG. 2.

Figure 3:
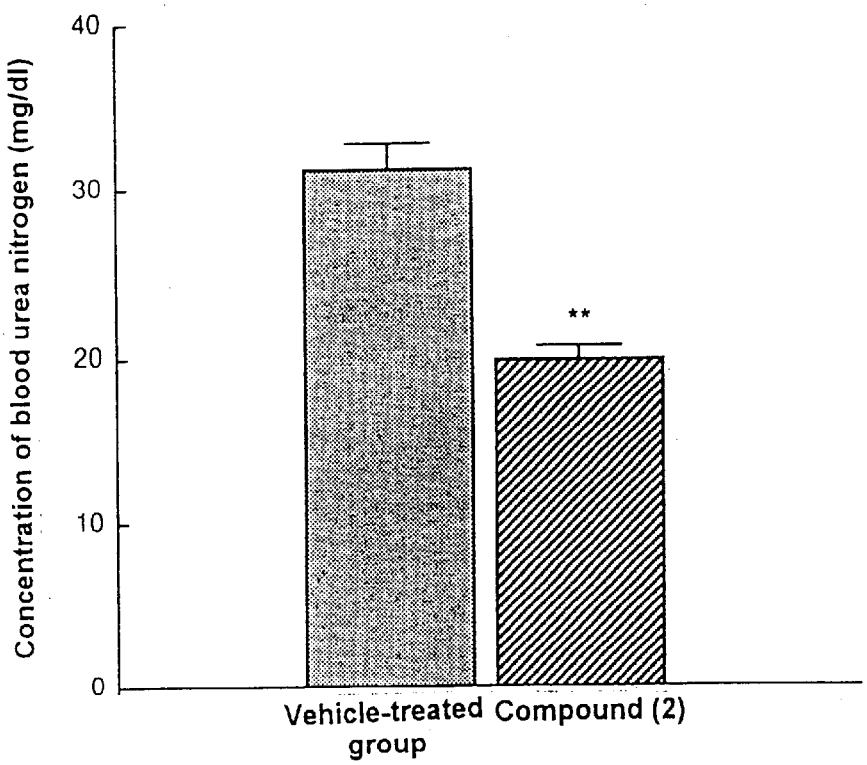
FIG. 3 shows the concentration of blood urea nitrogen in non-treated group and test compound-treated one 5 days after the initiation of experiment.
Figure 4:
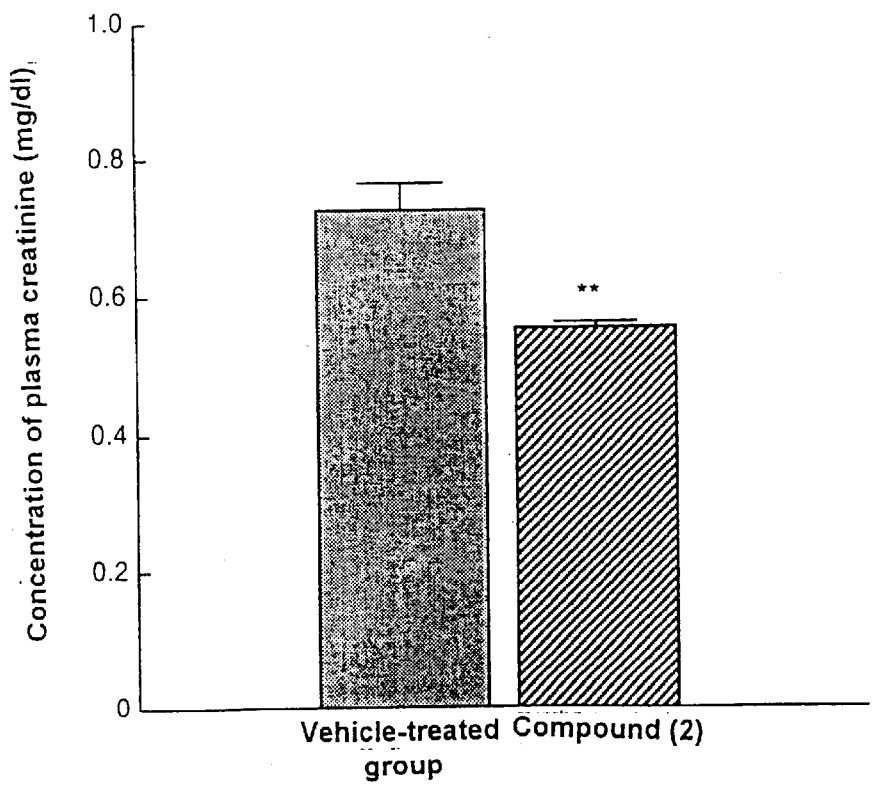
FIG. 4 shows the concentration of plasma creatinine in non-treated group and test compound-treated one 5 days after the initiation of experiment.

On the follow-up day (day 5), blood samples were collected and processed for the determination of blood urea nitrogen and plasma creatinine. Concentration of blood urea nitrogen was measured with Creatinine-test Wako (Wako Zyunyaku). The result is shown in FIG. 3. Concentration of plasma creatinine was determined with Urea nitrogen B-test Wako (Wako Zyunyaku). The result is shown in FIG. 4.

TEST EXAMPLE 2

Figure 5:
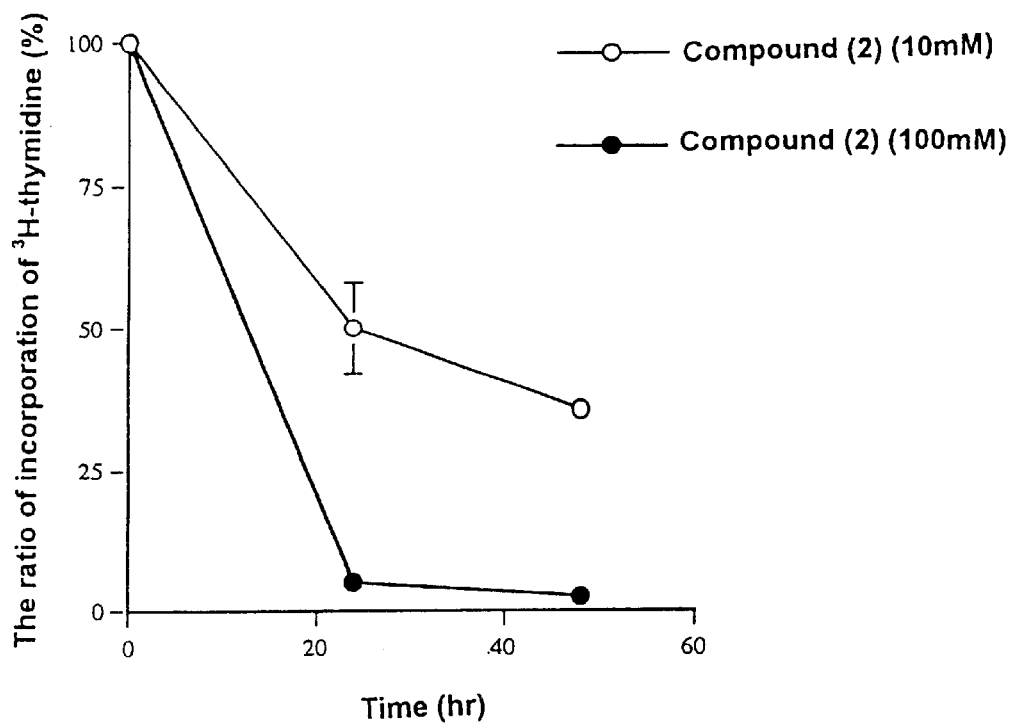
FIG. 5 shows the ratio of $^3$H-thymidine incorporation with time course varying with the concentration of test compound to investigate the influence on the proliferation of cultured mesangial cells.

Mesangial cells isolated from glomeruli of male Wistar rats aged 4 weeks old were plated on wells of a 96-well tissue culture plate at a density of 1000 cells per well and cultibated in RPMI medium containing 20% fetal calf serum for 24 hours. Following incubation for 20 or 44 hours, $^3$H-thymidine (100000 dpm/well) was added in the cell-culture medium. Four hours later, cultured mesangial cells were washed followed by cell lysis with 0.1% SDS and deoxycholate (0.1 mg/ml). Measurement of incorporation of $^3$H-thymidine was determined by counting radio activity with liquid scintillation counter, and the ratio of incorporation was calculated. The result is shown in FIG. 5.

From the results summarized in FIG. 1 and Table 12, it has been proved that the amount of urinary protein excretion in test compound-treated group decrease significantly. It is known that the increase of urinary protein excretion is well associated with damaged glomeruli (as same as in human), therefore, proteinuria is a good indicator of renal dysfunction. After the injection of E30, the amount of the urinary protein excretion remarkably increased. Renal function in rats with E30 monoclonal antibody became detrimental. In test compound-treated group, urinary protein excretion was significantly suppressed, indicating that the compound served as a preventing or treating agent against glomerular injury.

As shown in FIG. 2, cell proliferation was suppressed in test compound-treated group. Extraordinary proliferation of mesangial cells are observed in glomeruli 5 days after a injection of monoclonal antibody (observation with light and electron microscopy). The proliferating cells could be detected by immunohistochemistry with PCNA antigen expressing during S phase within the cell cycle. Therefore, comparison study of the number of PCNA positive cells per single glomerulus between vehicle-treated group and test compound-treated one provided the evidence as described above.

FIG. 3 shows that concentration of blood urea nitrogen in test compound-treated group decreased significantly. Therefore, decrease in renal function (glomerular filtration rate) was modified by the treatment of test compound, indicating that the compound served as a preventing or treating agent against glomerular injury.

FIG. 4 shows that concentration of plasma creatinine in test compound-treated group decreased significantly. Therefore, decrease in renal function (glomerular filtration rate) was modified by the treatment of test compound, indicating that the compound served as a preventing or treating agent against glomerular injury.

FIG. 5 shows that the test compound inhibited serum-induced mesangial proliferation in a dose-dependent manner. This experiment was designed to define whether the inhibitory effect of the test compound on mesangial proliferation, as shown in FIG. 2, was originated from its direct effect (on the cells) or not.

As shown in the above results, it is clearly recognized that the compounds of the present invention suppress the amount of urinary protein excretion and the proliferation of mesangial cells mostly observed in glomerulopathy. The state of a disease occurred in these experimental models is similar to the human glomerulonephritis and diabetic nephropathy. Therefore, the compounds of the present invention are useful for a composition for preventing or treating glomerulonephritis and diabetic nephropathy.

TEST EXAMPLE 3
Assay for Inhibitory Activities of MMP-9 and MMP-2

The enzymatic activity was analyzed on the method described by Knight, C. G., et al. (C. Graham Knight., Frances Willenbrock and Gillian Murphy: A novel coumarin-labelled peptide for sensitive continuous assays of the matrix metalloproteinases. FEBS Lett., 296 (1992) 263–266).

MMP-9 was purified by using a combination of procedures described in previous reports as follows. Yasunori Okada, Yukio Gonoji, Katsumi Naka, Katsuro Tomita, Isao Nakanishi, Kazushi Iwata and Taro Hayakawa: Matrix metalloproteinase 9 (92-kDa gelatinase/type IV collagenase) from HT1080 human fibrosarcoma cells. Purification and activation of the precursor and enzymic properties. J. Biol. Chem., 267 (1992) 21712–21719. Yasunori Okada, Tatsuhisa Morodomi, Jan J, Enghild, Ko Suzuki, Atsushi Yasui, Isao Nakanishi, Guy Salvesen and Hideaki Nagase: Matrix metalloproteinase 2 from human rheumatoid synovial fibroblasts. Purification and activation of the precursor and enzymic properties. Eur. J. Biochem. 194 (1990) 721–730. Robin V Ward, Rosalind M Hembry, John J Reynolds and Gillian Murphy: The purification of tissue inhibitor of metalloproteinase-2 from its 72 kDa progelatinase complex. Biochem. J. 278 (1991) 179–187.

Briefly, human fibrosarcoma ATCC HT1080 cell line was cultured to confluent in Dulbecco's Modified Medium (DMEM) containing 10% fetal-calf serum at 37° C. for 48 hours. Subsequently, the medium of confluent culture was changed to serum-free DMEM medium. To obtain MMP-9, Phorbol-12-myristate-13-acetate (TPA) must be added to this serum-free DMEM medium at a concentration of 50 ng/ml. The TPA treated medium was centrifuged at 3000 rpm for 15 min and the supernatant was concentrated to 450 ml by a Toyo-Roshi UP-20 apparatus with an ultrafiltration membrane. Then, proMMP-9 in this concentrated solution was purified by using columns of Gelatin-Sepharose and Concanavalin A-Sepharose. The pool containing proMMP-9 was dialyzed, concentrated (Toyo-Roshi UP-20) and applied to columns of Sephacryl S-200 and Green A matrix for the separation from TIMPs. The obtained proMMP-9 fraction was activated by TPCK-Trypsin (final conc. 3 $\mu g/\mu l$ reaction mix.) for the assay.

MMP-2 was purchased from Yagai (Yamagata pref., Japan).

MOCAc-Pro-Leu-Gly-Leu-A2pr(Dnp)-Ala-Arg-NH$_2$ as a substrate was purchased from Petide Institute(Osaka pref., Japan). This substrate was dissolved in DMSO at a concentration of 1 mM.

Reaction buffer consists of 50 mM Tris-HCl buffer (pH 7.5) containing 10 mM CaCl$_2$, 0.3 M NaCl, 0.005% Brij35 and 0.01% NaN$_3$.

Assay Method of Inhibitory Activity Against MMP-9:

1.0 $\mu l$ of a tested compound in DMSO is added to 48.0 $\mu l$ of a reaction buffer containing 0.08 $\mu l$ of an enzyme solution. After standing for 60 minutes at room temperature, the reaction was started by adding 1.0 $\mu l$ of a substrate solution. After incubation for 60 minutes at room temperature, 100 $\mu l$ of 3% (v/v) AcOH for reaction stopping and measured a fluorescence with excitation and emission at 320 nm and 405 nm, respectively (Spectrophotofluorometer; Fluoroscan Ascent (Labsystem)).

Assay Method of Inhibitory Activity Against MMP-2:

1.0 $\mu l$ of a tested compound in DMSO is added to 48.0 $\mu l$ of a reaction buffer containing 0.05 $\mu l$ of an enzyme solution. After standing for 60 minutes at room temperature, the reaction was started by adding 1.0 $\mu l$ of a substrate solution. After incubation for 60 minutes at room temperature, 100 $\mu l$ of 3% (v/v) AcOH for reaction stopping and measured a fluorescence with excitation and emission at 320 nm and 405 nm, respectively (Spectrophotofluorometer; Fluoroscan Ascent (Labsystem)).

The measurement of the inhibitory activities (IC$_{50}$) was carried out in a following four methods;

A) Reaction with substrate, enzyme and inhibitor
B) Reaction with substrate and inhibitor, without enzyme
C) Reaction with substrate and enzyme, without inhibitor
D) Reaction with substrate only IC$_{50}$ values were calculated by using a following formula and each fluorescence values of above four methods (A to D).

$$\% \text{ inhibition} = \{1-(A-B)/(C-D)\} \times 100$$

IC$_{50}$ means the concentration required to inhibit 50% of the enzyme activity. The results are shown in Table 13.

TABLE 13

| Compound No. | IC$_{50}$ (MMP-2) ($\mu$M) | IC$_{50}$ (MMP-9) ($\mu$M) |
|---|---|---|
| 87 | 0.003687 | 0.01 |
| 95 | 0.0107 | 0.019 |
| 96 | 0.0015 | 0.0362 |
| 97 | 0.01557 | 0.1360 |
| 98 | 0.0953 | 0.787 |
| 99 | 0.00459 | 0.04926 |
| 103 | 0.00612 | 0.0278 |
| 104 | 0.00202 | 0.01867 |
| 105 | 0.04137 | 0.3042 |
| 106 | 0.02827 | 0.1037 |
| 107 | 0.00351 | 0.00825 |
| 108 | 0.00992 | 0.0312 |
| 109 | 0.00471 | 0.0132 |
| 110 | 0.0257 | 0.0947 |
| 111 | 0.01069 | 0.1042 |
| 112 | 0.02842 | 0.1263 |
| 113 | 0.005701 | 0.07179 |
| 114 | 0.02778 | 0.3161 |
| 115 | 0.181 | 4.61 |
| 116 | 0.01224 | 0.09401 |
| 117 | 0.002619 | 0.03098 |
| 118 | 0.002159 | 0.06161 |
| 119 | 0.001693 | 0.04549 |
| 120 | 0.0009195 | 0.005815 |
| 121 | 0.000561 | 0.148 |

FORMULATION EXAMPLE

FORMULATION EXAMPLE 1

Granules are prepared using the following ingredients.

| Ingredients | |
|---|---|
| The compound represented by the formula (I) | 10 mg |
| Lactose | 700 mg |
| Corn starch | 274 mg |
| HPC-L | 16 mg |
| | 1000 mg |

The compound represented by the formula (I) and lactose were made pass through a 60 mesh sieve. Corn starch was made pass through a 120 mesh sieve. They were mixed by a twin shell blender. An aqueous solution of HPC-L (low mucosity hydroxypropylcellulose) was added to the mixture and the resulting mixture was kneaded, granulated (by the extrusion with pore size 0.5 to 1 mm mesh), and dried. The dried granules thus obtained were sieved by a swing sieve (12/60 mesh) to yield the granules.

FORMULATION 2

Powders for filling capsules are prepared using the following ingredients.

| Ingredients | |
|---|---|
| The compound represented by the formula (I) | 10 mg |
| Lactose | 79 mg |
| Corn starch | 10 mg |
| Magnesium stearate | 1 mg |
| | 100 mg |

The compound represented by the formula (I) and lactose were made pass through a 60 mesh sieve. Corn starch was made pass through a 120 mesh sieve. These ingredients and magnesium stearate were mixed by a twin shell blender. 100 mg of the 10-fold trituration was filled into a No. 5 hard gelatin capsule.

FORMULATION 3

Granules for filling capsules are prepared using the following ingredients.

| Ingredients | |
|---|---|
| The compound represented by the formula (I) | 15 mg |
| Lactose | 90 mg |
| Corn starch | 42 mg |
| HPC-L | 3 mg |
| | 150 mg |

The compound represented by the formula (I) and lactose were made pass through a 60 mesh sieve. Corn starch was made pass through a 120 mesh sieve. After mixing them, an aqueous solution of HPC-L was added to the mixture and the resulting mixture was kneaded, granulated, and dried. After the dried granules were lubricated, 150 mg of that were filled into a No. 4 hard gelatin capsule.

FORMULATION 4

Tablets are prepared using the following ingredients.

| Ingredients | |
|---|---|
| The compound represented by the formula (I) | 10 mg |
| Lactose | 90 mg |
| Microcrystal cellulose | 30 mg |
| CMC-Na | 15 mg |
| Magnesium stearate | 5 mg |
| | 150 mg |

The compound represented by the formula (I), lactose, microcrystal cellulose, and CMC-Na (carboxymethylcellulose sodium salt) were made pass through a 60 mesh sieve and then mixed. The resulting mixture was mixed with magnesium stearate to obtain the mixed powder for the tablet formulation. The mixed powder was compressed to yield tablets of 150 mg.

Industrial Applicability

The sulfonamide derivatives of the present invention inhibit the initiation and progression of the glomerulopathy, especially glomerulonephritis and diabetic nephropathy and are useful as the treating or preventing agent.

What is claimed is:

1. A method for treating or preventing glomerulopathy which comprises administering an effective amount of a compound of Formula (I) and pharmaceutically acceptable carrier:

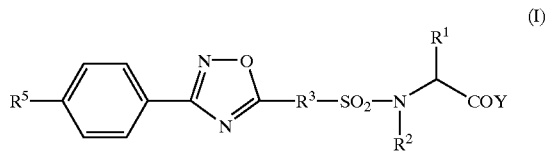

wherein $R^1$ and $R^2$ are each independently hydrogen atom, optionally substituted lower alkyl, optionally substituted aryl, optionally substituted aralkyl, optionally substituted heteroaryl or optionally substituted heteroarylalkyl;

$R^3$ is 1,4-phenylene or 2,5-thiophendiyl;

$R^5$ is hydrogen atom, hydroxy, optionally substituted lower alkyloxy, mercapto, lower alkylk thio, cycloalkyl, halogen, carboxy, lower alkyloxycarbonyl, nitro, cyano, lower hgaloalkyl, aryloxy, optionally substituted amino, guanidino, optionalyl substituted lower alkyl, lower alkenyl, lower alkynyl, acyl, acyoxy, —$CONR^AR^B$, —$N(R^C)COR^D$ (wherein $R^A$, $R^B$ and $R^C$ are the same or different selected from hydrogen atom, lower alkyl and aralkyl;

$R^D$ is lower alkyl, aryl or aralkyl), optionally substituted non-aromatic heterocyclic group, or optionally substituted heteroaryl;

Y is NHOH or OH;

its optically active substance, their pharmaceutically acceptable salt or hydrate thereof.

2. A method for treating or preventing glomerulopathy which comprises administering an effective amount of a compound of Formula (II) and pharmaceutically acceptable carrier:

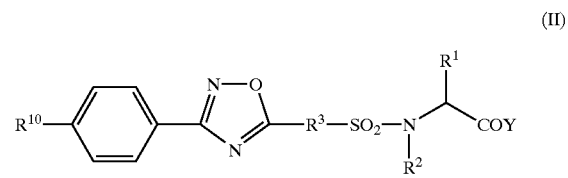

wherein $R^1$, $R^2$, $R^3$ and Y are as defined in claim 1; and $R^{10}$ is hydrogen atom, optionally substituted lower alkyloxy, lower alkylthio, halogen, optionally substituted amino, optionally substituted lower alkyl or optionally substituted non-aromatic heterocyclic group;

its optically active substance, their pharmaceutically acceptable salt of hydrate thereof.

3. A method for treating or preventing glomerulopathy of any one of claims 1 or 2, wherein $R^1$ is hydrogen atom, methyl, i-propyl, i-butyl, optrionally substituted benzyl, optionally substituted indol-3-ylmethyl or phenylaminocarbonylethyl.

4. A method for treating or preventing glomerulopathy of any one of claims 1 or 2, wherein $R^1$ is i-propyl, benzyl, or indol-3-ylmethyl.

5. A method for treating or preventing glomerulopathy of any one of claims 1 or 2, wherein $R^2$ is a hydrogen atom.

6. A method for treating or preventing glomerulopathy of any one of claims 1 or 2, wherein Y is OH.

7. A method for treating or preventing glomerulopathy of any one of claims 1 or 2, wherein glomerulopathy is glomerulonephritis.

8. A method for treating or preventing glomerulopathy of any one of claims 1 or 2, wherein glomerulopathy is diabetic nephropathy.

9. A compound of formula (III):

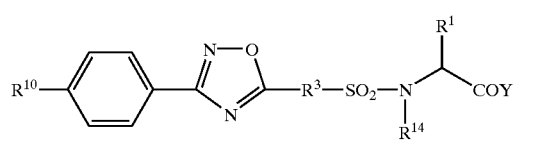

(III)

wherein $R^1$ hydrogen atom, optionally substituted lower alkyl, optionally substituted aryl, optionally substituted aralkyl, optionally substituted heteroaryl or optionally substituted heteroarylalkyl, Y is NHOH or OH, $R^{10}$ is hydrogen atom, optionally substituted lower alkyloxy, lower alkylthio, halogen, optionally substituted amino, optionally substituted lower alkyl or optionally substituted non-aromatic heterocyclic group; $R^3$ is 1,4-phenylene or 2,5-thiophendiyl and $R^{14}$ is hydrogen atom or lower alkyl, its optically active substance, their pharmaceutically acceptable salt, or hydrate thereof.

10. A pharmaceutical composition comprising a compound of claim 9.

11. A method of inhibiting matrix metalloproteinase comprising administering to a parent in need thereof a therapeutically effective amount of a compound of claim 9.

12. A method of inhibiting type IV collagenase comprising administering to a patient in need thereof a therapeutically effective amount of a compound of claim 9.

13. A method of treating or preventing glomerulopathy which comprises administering an effective amount of a compound of claim 9 and a pharmaceutically acceptable carrier.

* * * * *

UNITED STATES PATENT AND TRADEMARK OFFICE
CERTIFICATE OF CORRECTION

PATENT NO.   : 6,423,729 B1
DATED        : July 23, 2002
INVENTOR(S)  : Hidetake Kurihara et al.

It is certified that error appears in the above-identified patent and that said Letters Patent is hereby corrected as shown below:

<u>Column 3,</u>
Lines 55-67, delete

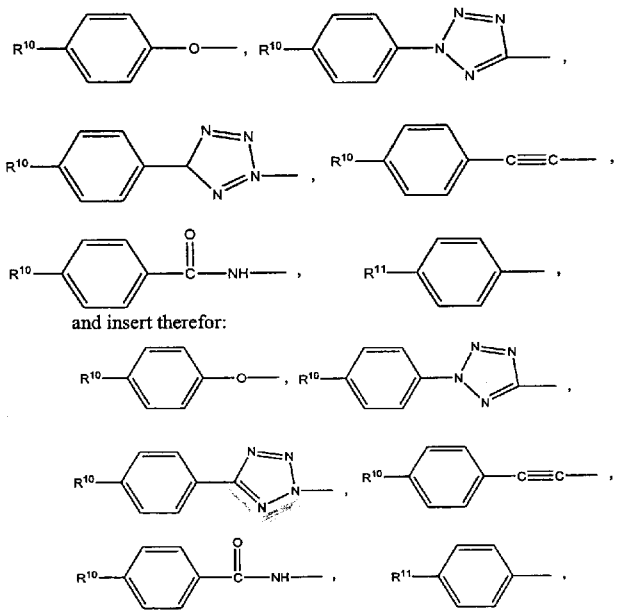

and insert therefor:

Table 1, Columns 25-26, compound 99, please delete the following:

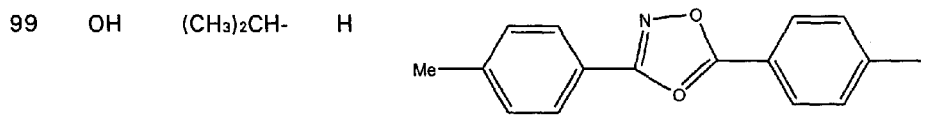

and insert therefor:

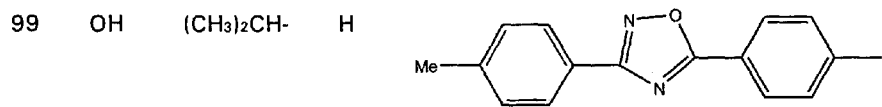

UNITED STATES PATENT AND TRADEMARK OFFICE
CERTIFICATE OF CORRECTION

PATENT NO.    : 6,423,729 B1
DATED         : July 23, 2002
INVENTOR(S)   : Hidetake Kurihara et al.

It is certified that error appears in the above-identified patent and that said Letters Patent is hereby corrected as shown below:

Table 2, Columns 31-32, compound 39, please delete the following:

39   OH   (CH$_3$)$_2$CH-   H   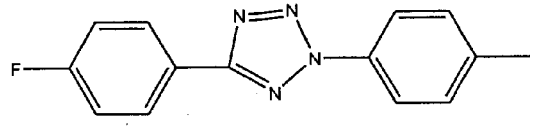

and insert therefor:

39   OH   (CH$_3$)$_2$CH-   H   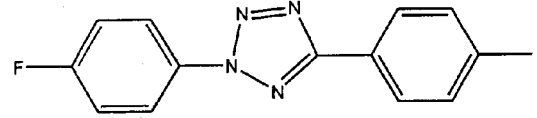

Signed and Sealed this

Twenty-seventh Day of May, 2003

JAMES E. ROGAN
*Director of the United States Patent and Trademark Office*